(12) United States Patent
Nakamura

(10) Patent No.: US 9,062,833 B2
(45) Date of Patent: Jun. 23, 2015

(54) MEDICAL LIGHT SOURCE DEVICE

(75) Inventor: Shoichi Nakamura, Nagano (JP)

(73) Assignees: ACP JAPAN CO., LTD., Tokyo (JP); Shoichi Nakamura, Higashichikuma-gun, Nagano (JP)

( * ) Notice: Subject to any disclaimer, the term of this patent is extended or adjusted under 35 U.S.C. 154(b) by 197 days.

(21) Appl. No.: 13/983,246

(22) PCT Filed: May 23, 2012

(86) PCT No.: PCT/JP2012/063211
§ 371 (c)(1),
(2), (4) Date: Aug. 1, 2013

(87) PCT Pub. No.: WO2013/084521
PCT Pub. Date: Jun. 13, 2013

(65) Prior Publication Data
US 2013/0314903 A1 Nov. 28, 2013

(30) Foreign Application Priority Data
Dec. 6, 2011 (JP) ................. 2011-267027

(51) Int. Cl.
*F21V 23/04* (2006.01)
*F21V 21/084* (2006.01)
*F21L 4/00* (2006.01)
(Continued)

(52) U.S. Cl.
CPC .............. *F21L 4/00* (2013.01); *F21W 2131/20* (2013.01); *Y02B 20/44* (2013.01); *H05B 33/0854* (2013.01); *H05B 33/089* (2013.01); *H05B 37/0227* (2013.01); *A61B 2019/521* (2013.01); *A61B 2019/5287* (2013.01); *F21V 23/003* (2013.01); *F21V 23/0492* (2013.01); *F21V 21/084* (2013.01); *F21W 2131/202* (2013.01); *F21V 23/04* (2013.01)

(58) Field of Classification Search
CPC ... F21V 23/003; F21V 23/04; F21V 23/0492; F21V 21/084; F21L 4/00; F21W 2131/20; F21W 2131/202; H05B 33/0854; H05B 33/089; A61B 2019/521; A61B 2019/5287
See application file for complete search history.

(56) References Cited

U.S. PATENT DOCUMENTS 2,539,104 A * 1/1951 Rodel ........................... 600/248
7,370,991 B1 * 5/2008 Ellis-Fant .................... 362/233
(Continued)

FOREIGN PATENT DOCUMENTS

JP 2002-298607 A 10/2002
JP 2006-107846 A 4/2006
(Continued)

*Primary Examiner* — Alan Cariaso
(74) *Attorney, Agent, or Firm* — Manabu Kanesaka

(57) ABSTRACT

A medical light source device worn on the body of an operator enables the application range to be set at a state displaced from the direction in which the body currently faces. An acceleration sensor 106 is attached to a holder 7 to put an illumination section 1 on the body of the operator, and detects a motion of the body of the operator. When an application-range center position setting switch 107b is operated, a position detecting section 108 detects a center position based on the acceleration information detected by the acceleration sensor 106, and an optical axis adjusting section 108 fixes the optical axis of the illumination section 1 to the detected center position. Then, the application angle of application light from the illumination section 1 is capable of being adjusted in a plurality of stages by an application control section 110.

13 Claims, 16 Drawing Sheets

(51) Int. Cl.
  *H05B 37/02* (2006.01)
  *F21V 23/00* (2015.01)
  *F21W 131/20* (2006.01)
  *H05B 33/08* (2006.01)
  *A61B 19/00* (2006.01)
  *F21W 131/202* (2006.01)

(56) References Cited

U.S. PATENT DOCUMENTS 7,824,052 B1 * 11/2010 Halm .......................... 362/105
2009/0146583 A1   6/2009 Bhadri 2009/0174348 A1 *  7/2009 Cugini et al. ............... 315/312
2009/0227847 A1 *  9/2009 Tepper et al. ............... 600/249
2010/0296285 A1 * 11/2010 Chemel et al. ............. 362/235
2011/0216548 A1 *  9/2011 Fritz et al. .................. 362/466

FOREIGN PATENT DOCUMENTS

| JP | 2006-185755 A | 7/2006 |
| JP | 2008-210547 A | 9/2009 |
| JP | 2009-293146 A | 12/2009 |
| JP | 4841013 B | 10/2011 |
| JP | 2011-218092 A | 11/2011 |

* cited by examiner

MEDICAL LIGHT SOURCE DEVICE

RELATED APPLICATIONS

The present application is National Phase of International Application No. PCT/JP2012/063211 filed May 23, 2012, and claims priority from Japanese Application No. 2011-267027, filed Dec. 6, 2011.

TECHNICAL FIELD

The present invention relates to a medical light source device for irradiating a treatment target portion with light in the medical treatment.

BACKGROUND ART

As a medical light source device used in the medical treatment (including operations), in order to enable an operator such as a medical doctor to increase a quantity of light applied to the treatment target part by oneself and secure sufficient brightness, it is known that the operator wears the light source device on the body such as the head and performs the medical treatment.

As such a light source device wearable on the body, a battery built-in type portable LED light is known which is provided with a clip capable of being put in a breast pocket or a brim of a cap of the operator (for example, see Patent Document 1).

Further, known are configurations of a cap with a light in which the LED light is attached to the brim and a battery separate from the light is also stored in the cap (for example, see Patent Documents 2 and 3).

PRIOR ART DOCUMENT

Patent Document

Patent Document 1: Japanese Patent Application Publication No. 2006-185755
Patent Document 2: Japanese Patent Application Publication No. 2008-210547
Patent Document 3: Japanese Patent Application Publication No. 2009-293146

DISCLOSURE OF INVENTION

Problems to be Solved by the Invention

However, in the light source device worn on the body, since the application direction is determined by facing the body toward the application target portion, it is not possible to make the direction in which the body faces and the application direction different from each other.

For example, in the case of the medical light source device such that the light source device is worn on the head of the body, the operator looks at the treatment part, the head thereby faces in the direction to irradiate the treatment part, the position at which the operator looks and the treatment part match each other at this point, and light is applied with this position being the center position of the illumination range. However, such a situation occurs that the operator lights without matching the center position of the application range and the treatment part during the medical treatment. In other words, the situation is the case of performing the medical treatment while checking the state of another part different from the treatment part, and at this point, when the another part is out of the application range, the operator needs to move the head to change the application range from the treatment part to the another part whenever the operator checks, and to perform extremely burdensome work.

Therefore, desired is a medical light source device that requires the operator only to change the eye line without moving the head to enable the another part to be within the application range even when the position of the head is not faced toward the another portion.

Further, in the medical treatment, for example, depending on the treatment such as cutting and suture of a blood vessel or minute portion and the like, there is a case that the operator wants to irradiate with a higher quantity of light only for a short time. However, in such a case, the operator concentrates the operator's fingers on the treatment part, and when the operator performs switch operation for switching the quantity of light, lacks concentration, and therefore, desired is a medical light source device that enables the operator to perform switch operation easily without using the fingers.

To solve the above-mentioned problems, it is an object of the present invention to provide a medical light source device that enables the application direction to be deflected in a state displaced from the direction in which the body faces by setting.

Then, it is another object to provide a medical light source device that enables switching of the quantity of light and illumination ON/OFF to be performed without performing switch operation with the fingers.

Means for Solving the Problem

To attain the above-mentioned objects, a medical light source device according to the present invention is a medical light source device that is worn on the body of an operator to apply light to a target portion of the medical treatment, and is characterized by having a holder to put an illumination section on the body of the operator, an acceleration sensor attached to the holder, a position detecting section that detects a center position to hold based on acceleration information detected by the acceleration sensor in setting the center position of an application range, and an optical axis adjusting section that sets an optical axis of the illumination section at the detected center position. It is a feature that the holder is to put the illumination section and the acceleration sensor on the head of the operator.

Moreover, the device is characterized by further having an application control section capable of adjusting an application angle of application light from the illumination section in a plurality of stages.

Then, the acceleration sensor is characterized by having an X axis and a Y axis that are mutually orthogonal, and being attached to the holder so that the X axis tracks a right-and-left axis of the operator and that the Y axis tracks a back-and-forth axis of the operator. At this point, it is a feature that attachment of the acceleration sensor to the holder is beforehand provided with an angle. The acceleration sensor is characterized by being a three-axis sensor further including a Z axis.

Further, the device is characterized by having a reset means for clearing the center position held in the position detecting sensor to cancel setting of the optical axis.

A medical light source device according to the invention is a medical light source device that is worn on the body of an operator to apply light to a target portion of the medical treatment, and is characterized by having a holder to put an illumination section on the body of the operator, a battery power supply section that supplies power to the illumination section, an acceleration sensor attached to the holder, a motion detecting section that detects a predetermined motion by the operator based on acceleration information, and a light quantity control section that controls an amount of current fed from the battery power supply section to the illumination section when the predetermined motion is detected.

Herein, it is a feature that the illumination section is provided with a light source having durability even when a passing current exceeds a rated value, and that the light quantity control section changes an average current value fed from the battery power supply section to the illumination section from a rated value to an increase value higher than the rated value only for a predetermined period in increasing the amount of current. At this point, the predetermined period is set based on a temperature increase time characteristic of the light source due to passage of the increase value of current. Alternatively, the predetermined period is set at a period during which a temperature of the light source does not exceed a maximum allowable value, based on the temperature increase time characteristic of the light source.

Further, it is a feature that a second acceleration sensor is attached to the holder, and that the light quantity control section switches a value of current fed to the illumination section to the rated value of current when the acceleration sensor detects acceleration of a predetermined value or more in performing control for feeding the increase value of current as the average current value fed to the illumination section.

It is another feature that the device is further provided with a voice recognition section that recognizes a voice uttered by the operator, and that the light quantity control section controls an amount of current fed to the illumination section based on either the recognized voice in the voice recognition section or the acceleration information.

Advantageous Effect of the Invention

According to the invention, the acceleration sensor is attached to the holder mounted with the illumination section, the center position of the application range of the illumination section is set at a position of the acceleration information due to a motion of the body at this point, and the direction of the body and the application direction are subsequently fixed to different states even when the body moves. By this means, in such a medical treatment that the treatment is performed while checking another part different from the treatment part, the operator is capable of checking both parts by changing the eye line while fixing the direction of the body, and is thereby capable of concentrating on the medical treatment.

Further, it is possible to adjust increase/decrease of the light quantity by a motion of the body of the operator detected by the acceleration sensor, the operator thereby does not need to operate the switch with the operator's fingers, and the invention thus provides the optimal light source device for use in medical practice.

BEST MODE FOR CARRYING OUT THE INVENTION

Embodiments of the present invention will be described below with reference to drawings.

Figure 7:
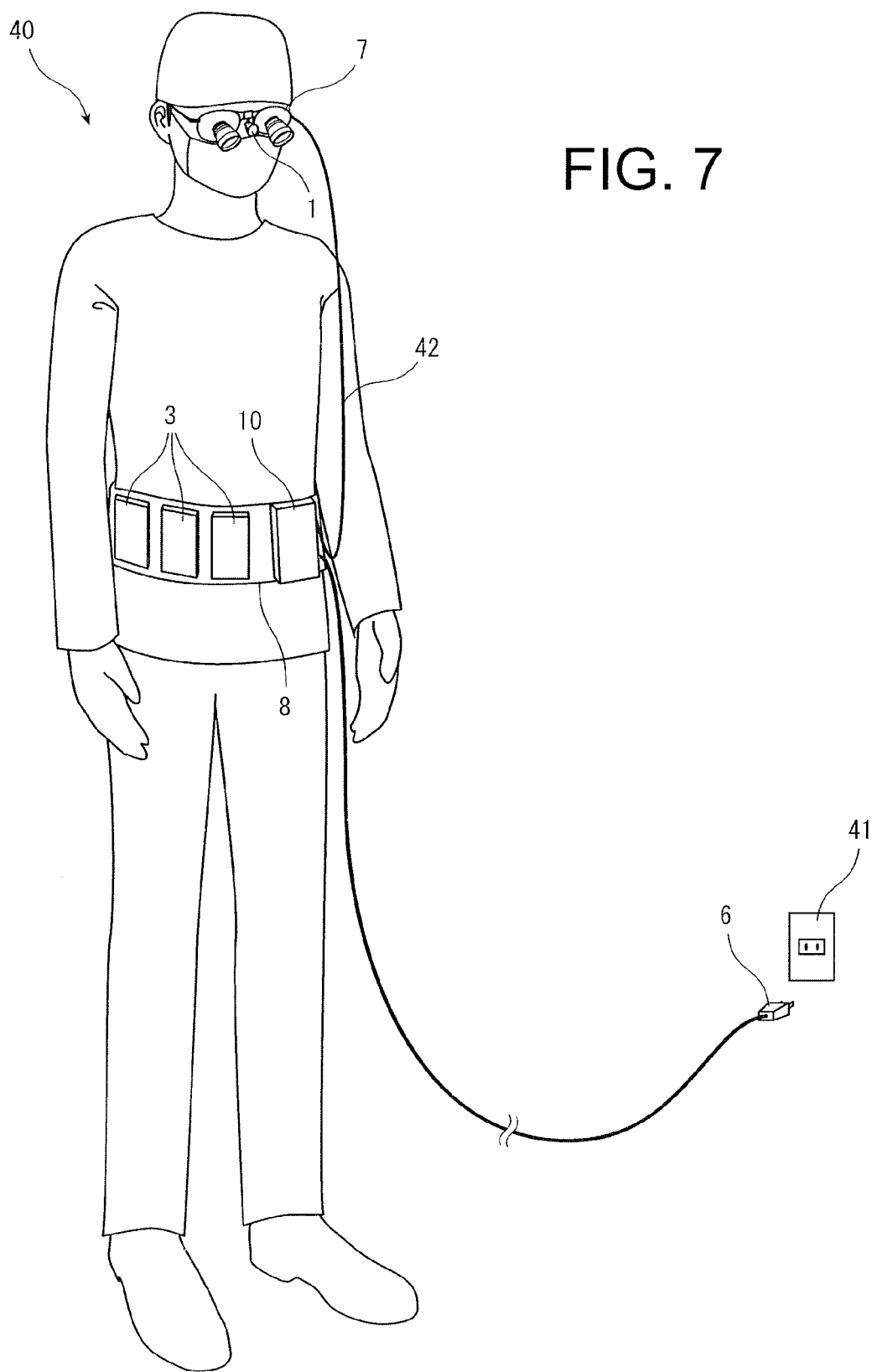
FIG. 7 is an explanatory view illustrating a state in which the medical light source device is worn according to the Embodiment of the invention.
Figure 9:
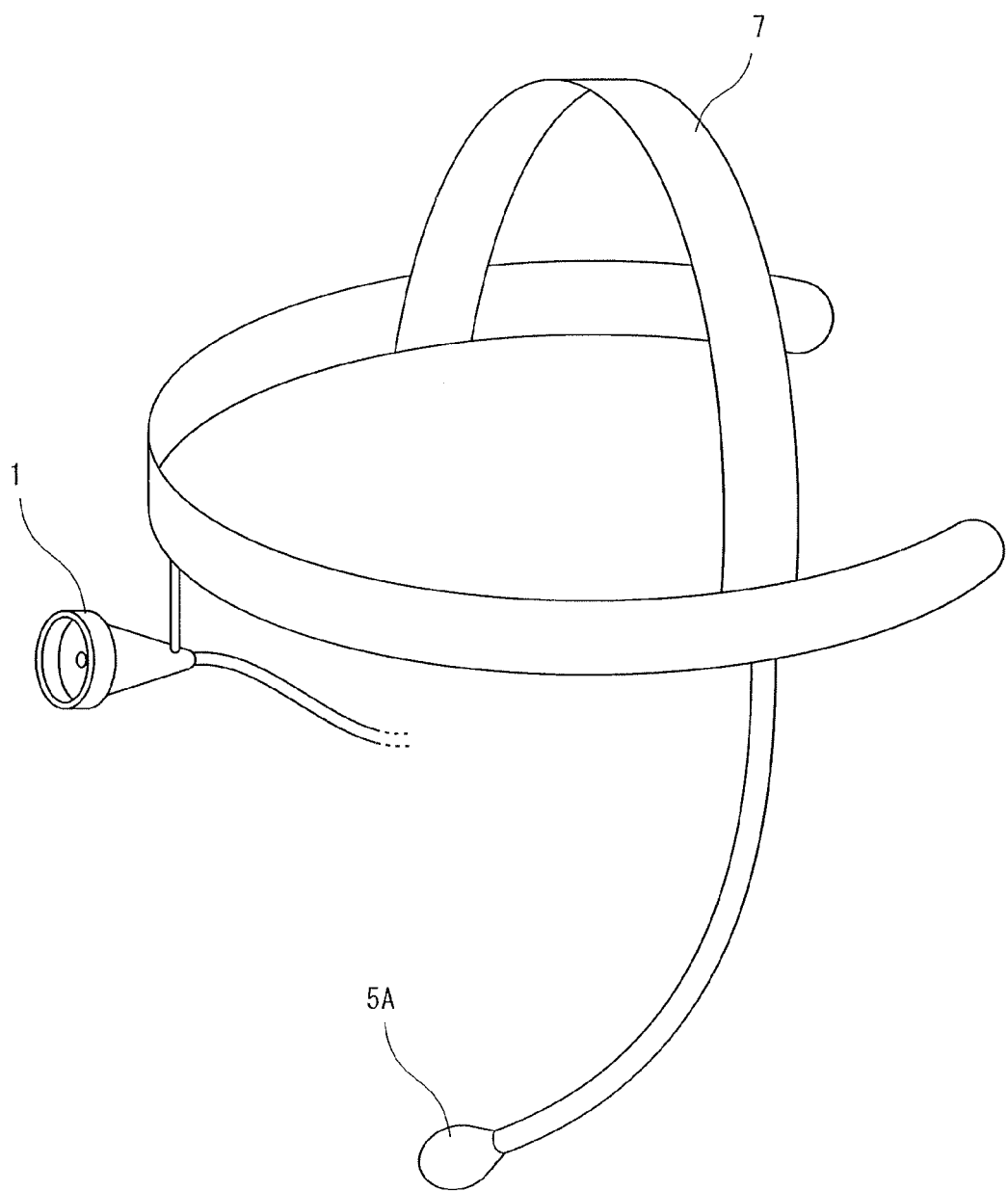
FIG. 9 is an explanatory view in which a head band is a holder of the medical light source device according to the Embodiment of the invention.

Described first is an external configuration of a medical light source device according to an Embodiment of the invention. FIG. 7 shows a state in which an operator 40 wears the medical light source device. An illumination section 1 is held with a binocular loupe worn by the operator 40 and is worn on the head of the operator 40. Accordingly, in this example, the binocular loupe is a holder 7. The holder 7 is not limited to such a binocular loupe, and may be a cap or a head band. FIG. 9 shows an example where a head band is the holder 7, and the illumination section 1 is attached to the head band. The head band is made of a resin member, is held on the head of the operator by its elasticity and can thereby be fixed. The head band is not limited to such a configuration, and also as the material, there are various modes such as cloth and rubber.

Figure 8:
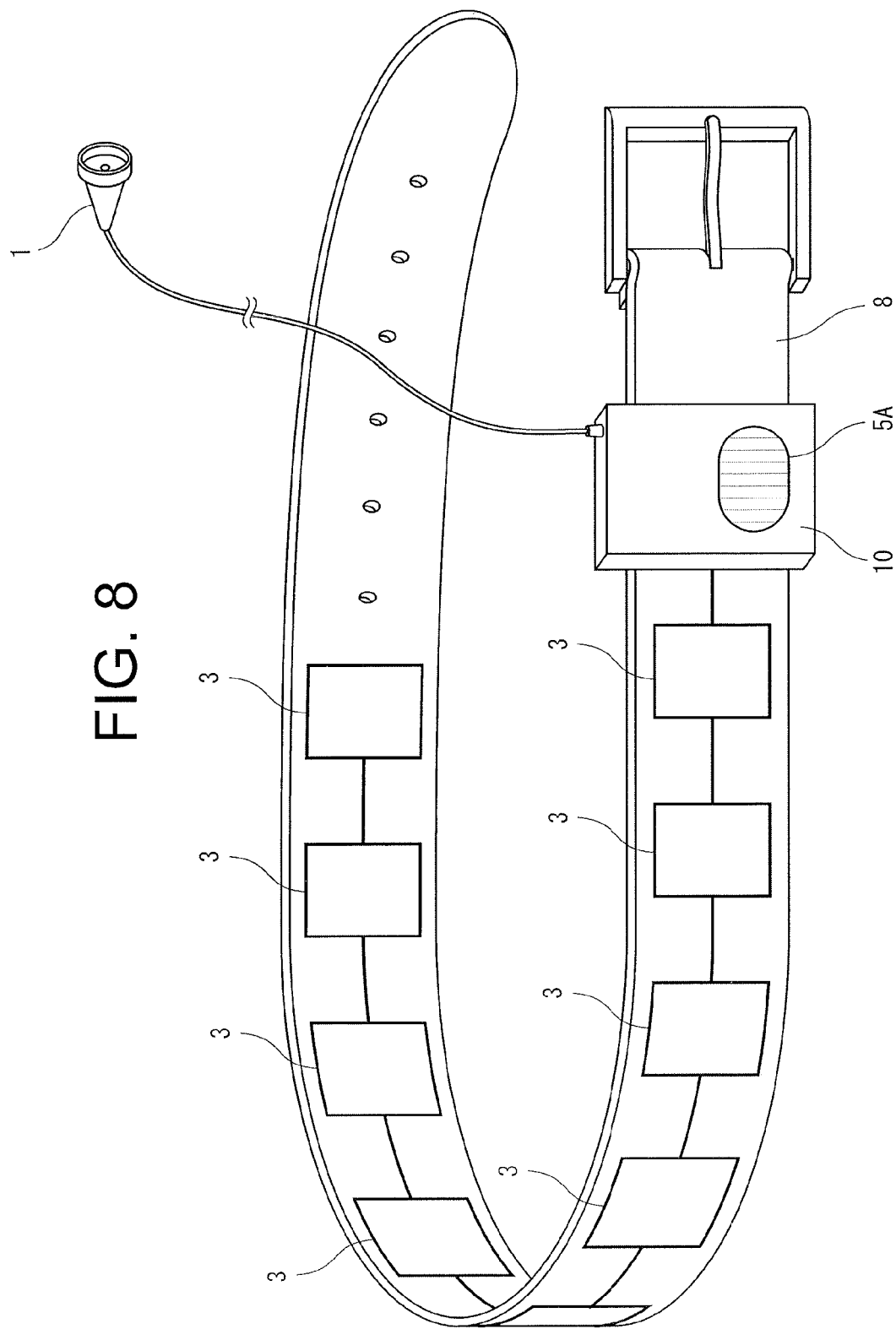
FIG. 8 is an explanatory view of a battery holding belt of the medical light source device according to the Embodiment of the invention.

Referring again to FIG. 7, as part of the body of the operator 40, in this example, a battery holding belt 8 is wound around the waist. To the battery holding belt 8 are attached a battery power supply section 11 (FIG. 1) provided with a plurality of mutually connected rechargeable batteries 3 and a control unit 10 as shown in FIG. 8.

The batteries 3 of the battery power supply section 11 are connected to the control unit 10, and the control unit 10 supplies a driving current to the illumination section 1 through a code 42 to control illumination operation. The batteries 3 of the battery power supply section 11 are not limited to a plurality of batteries, and there is a case that a single large-sized battery 3 is allowed as long as the battery 3 is capable of supplying stable power to the illumination section 1 over a long time, but even such a heavy battery is capable of being worn on part of the body by being attached to the battery holding belt 8.

Further, the control unit 10 performs charging control on the batteries 3 when a charger 6 with a plug inserted therein is connected to an outlet 41, and is capable of performing illumination operation by the illumination section 1 while charging the batteries 3.

Thus, the operator is capable of performing the medical treatment while holding the batteries 3 with the battery holding belt 8 attached to part of the body, and the device is suitable as a medical light source device required of long-duration medical treatment. Further, it is also possible to perform work while charging.

In the above-mentioned medical light source device, usually, the application direction of the illumination section 1 matches with the direction in which the body (head, in this example) faces, and the invention is to enable the application direction to be deflected in a state displaced from the direction in which the body faces by setting.

Figure 13:
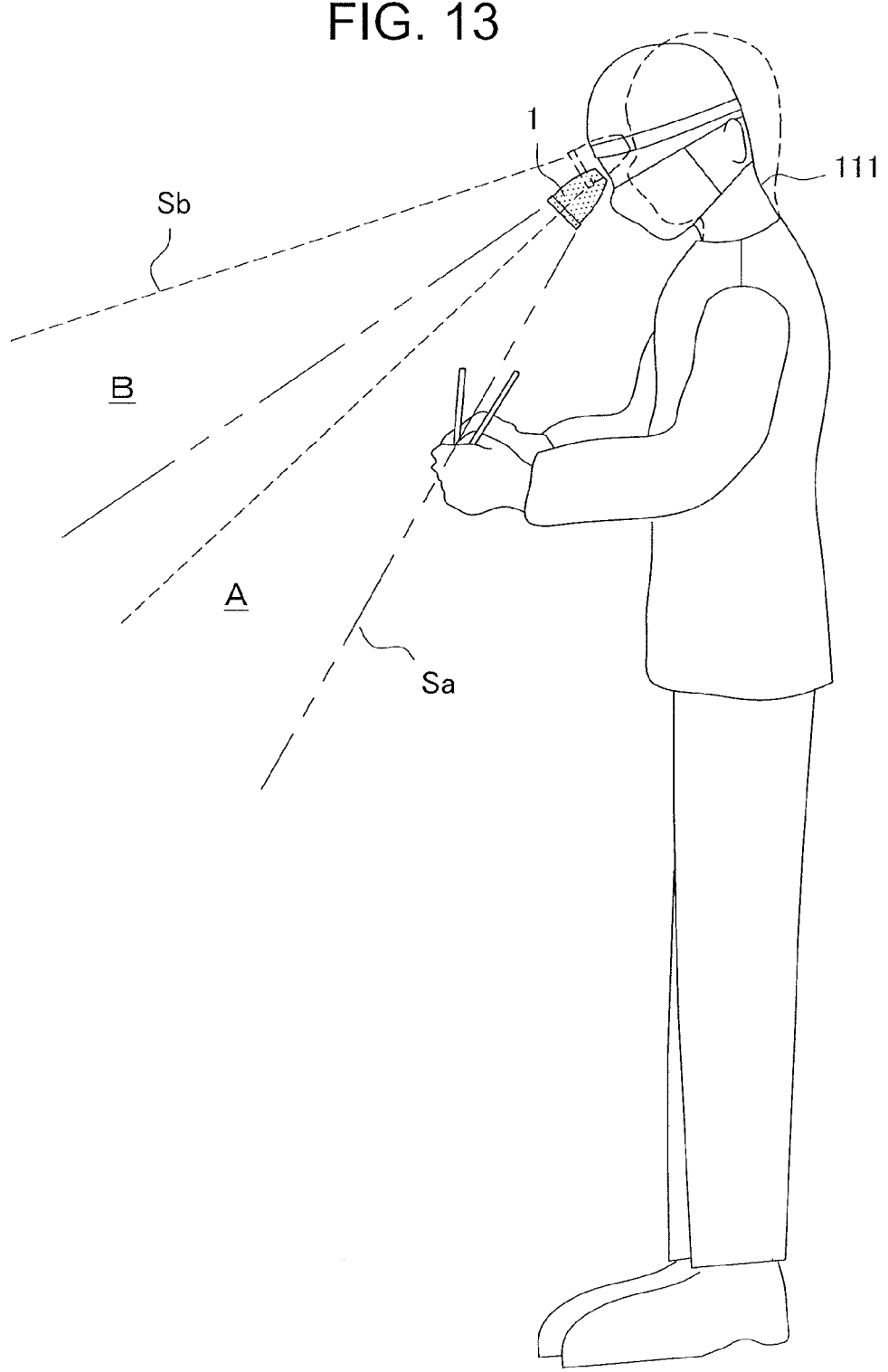
FIG. 13 is an explanatory view illustrating a state in which an operator changes an application range corresponding to an object.

Referring to FIG. 13, the invention will be specifically described. The illumination section 1 worn on the head 111 of the operator with the holder 7 applies light in the application range Sa shown by solid lines in accordance with the posture such that the operator stares at a target portion A to perform the medical treatment. At this point, when the operators needs to perform the treatment while checking a target portion B so as to perform the medical treatment on the target portion A, and wants to change the application range to a range Sb shown by dotted lines, the operator once moves the eye line from the target portion A to the target portion B, sets the position of the eye line at the position of the optical axis of the illumination section 1, and thereby holds a state in which the application direction of the illumination section 1 is directed toward the target portion B even when the eye line is returned to the target portion A.

At this point, an acceleration sensor detects the motion of the head 111 that changes the eye line from the target portion A to the target portion B, the optical axis is set with the position indicated by acceleration information being a center position of the application range by the illumination section 1, and it is thereby possible to deflect in a state displaced from the direction in which the body faces. Then, by storing the detected acceleration information, the application direction and the direction in which the body faces light always undergo deflection in a certain relationship.

Figure 14:
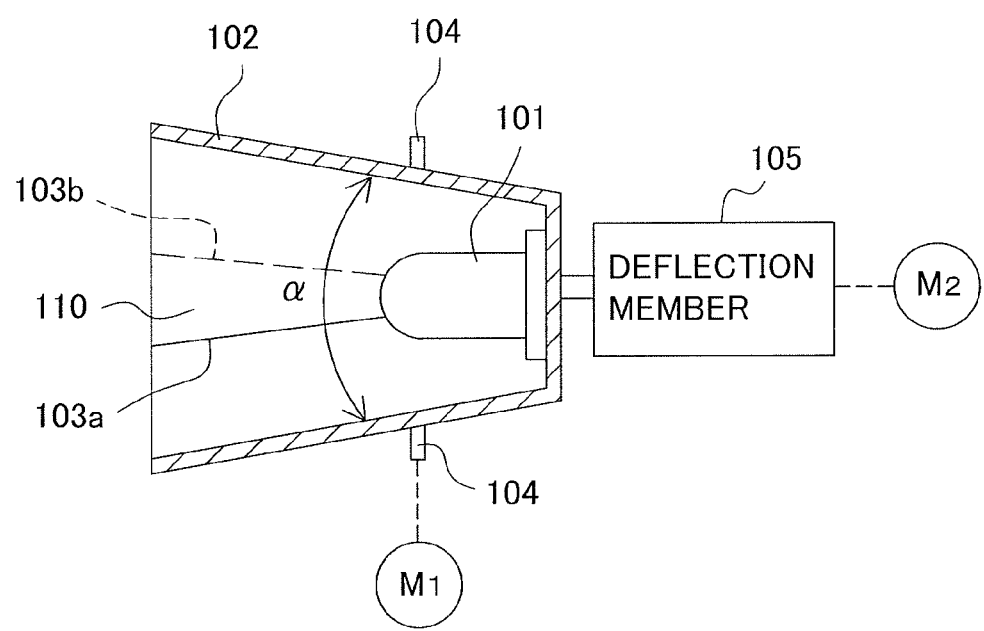
FIG. 14 is an explanatory view showing a side cross section of a configuration of an illumination section allowed to change the application direction and the application range.

As shown in FIG. 14, deflection of the application direction by the illumination section 1 is achieved by displacing the optical axis angle of a light source element 101 vertically, horizontally or circularly by 360 degrees with a deflection member 105. By this means, to check the target portion B while treating the target portion A, the operator does not need to move the head 111 every time, is required only to change the eye line, and is capable of concentrating on the medical treatment.

Further, when the target portion A goes out of the application range Sb by changing the application range from Sa to Sb, the application angle is expanded so as to include the target portion A to widen the application range Sb. As shown in FIG. 14, it is possible to expand the application angle by increasing an aperture angle α of a reflector 102 that is to apply light from the light source element 101 toward the object. For example, as shown in FIG. 14, a cut is provided along the optical axis direction in a part of a reflecting surface of the reflector 102 having the conical shape, the reflector 102 is tightened and loosened in the center direction from the outside with a tightening member 104 to adjust the width of an overlapping portion 110 of opposite end portions 103*a* and 103*b* of the reflector 102 with the cut made, and it is thereby possible to adjust the aperture angle α.

Figure 10:
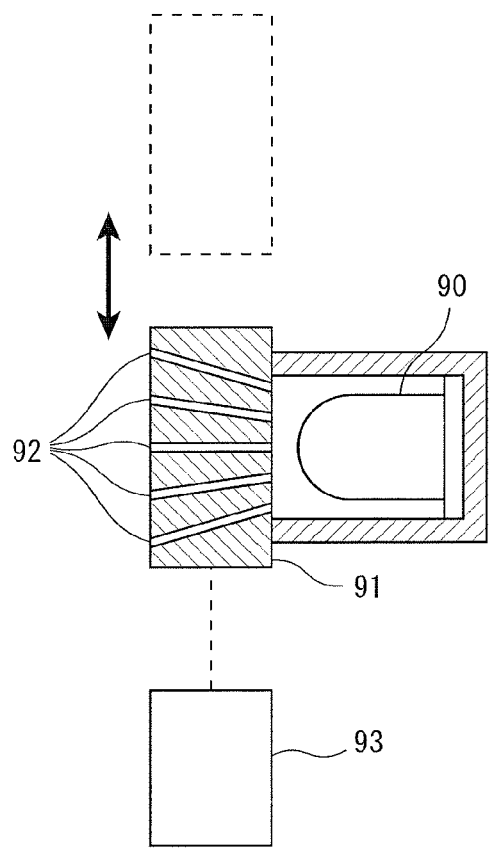
FIG. 10 is a schematic explanatory view showing a section along the application direction of light of a configuration for switching light from a light source between diffusion and convergence.

It is also possible to expand the application angle by adjusting a viewing angle of application light. An example of a configuration for adjusting a viewing angle of light will be schematically described with reference to FIG. 10. A diffusing member 91 provided with a plurality of slits 92 that diffuses light from a light source 90 by reflecting incident light is disposed in front of the light source 90 on the light output side. The diffusing member 91 is made movable between a solid-line position and a dotted-line position on the light output surface of the light source 90 by driving force of a driving section 93 using a motor or solenoid, and by shifting the diffusing member 91 to the position of solid line or dotted lines with the drive section 93, it is possible to widen or narrow the viewing angle of light of the light source 90.

Further, there is a configuration for switching between convergence light and diffusion light with a liquid crystal shutter. In this case, response is high, and it is possible to switch instantaneously.

Figure 15:
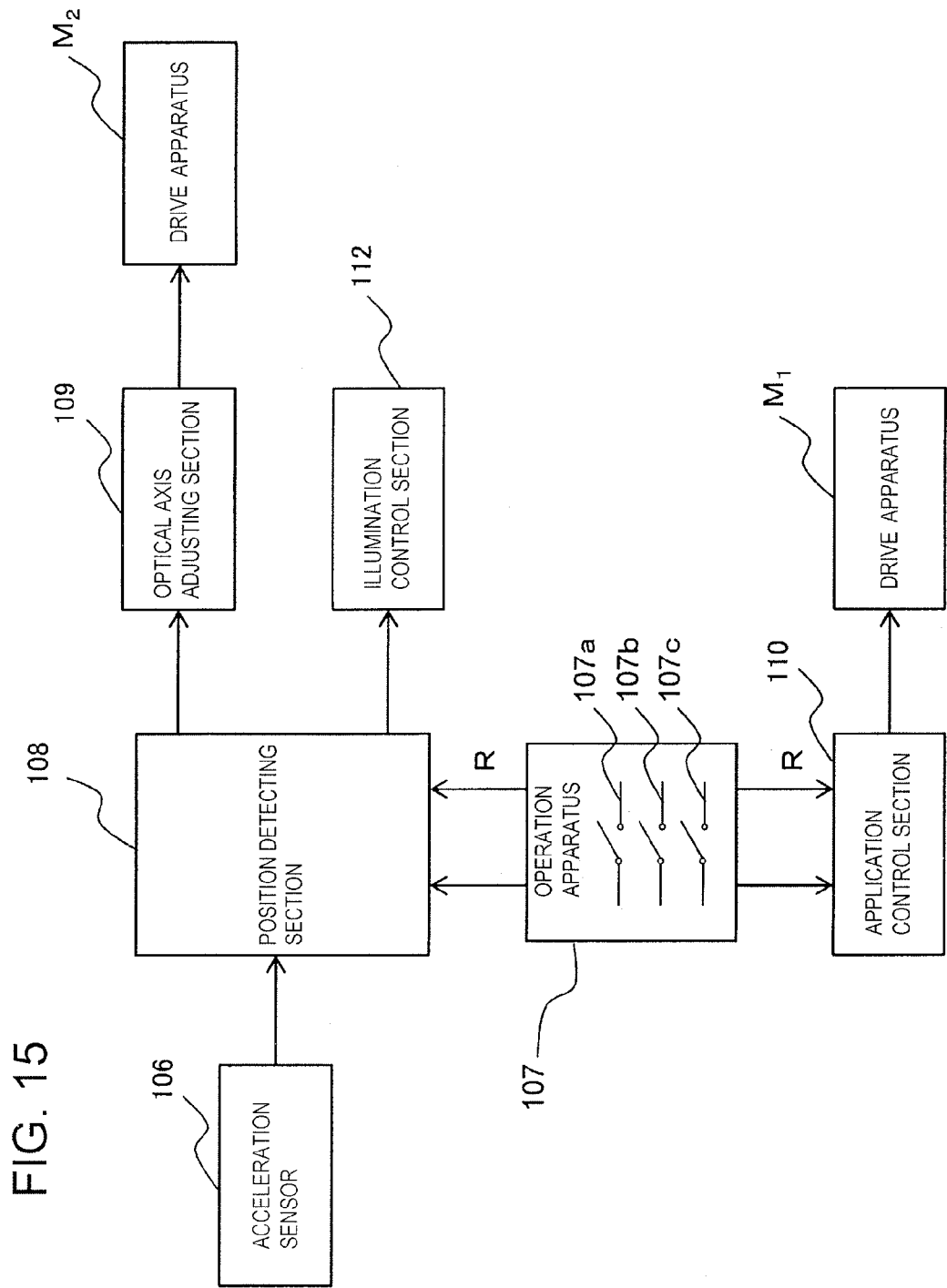
FIG. 15 is a functional block diagram to explain control for changing the application direction and the application range of the illumination section.
Figure 17:
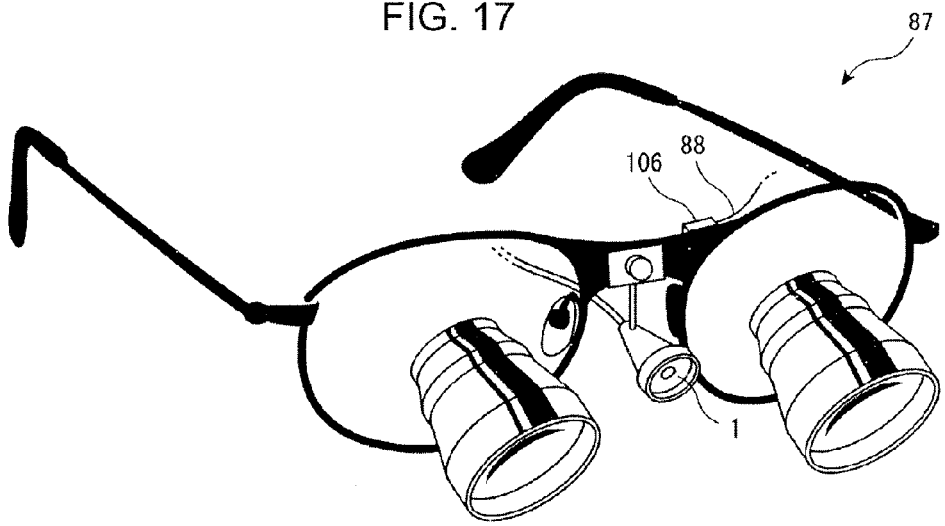
FIG. 17 is an explanatory view of a configuration in which the acceleration sensor is attached to a binocular loupe.

FIG. 15 is a functional block diagram to explain a change of the application range by the illumination section 1. An acceleration sensor 106 is attached to the holder 7 together with the illumination section 1, and is thereby capable of capturing a motion of the operator. FIG. 17 shows an example in which the acceleration sensor 106 is attached to a binocular loupe 87.

As the acceleration sensor 106, it is possible to use various kinds including the mechanical type, optical type and semiconductor type, and as a medical light source device with a binocular loupe, cap, head band or the like put on the head of the operator as the holder 7, the semiconductor type is optimal in terms of making the size smaller.

Then, the acceleration sensor 106 is a two-axis sensor having mutually orthogonal X axis and Y axis, is attached to the holder 7 so that the X axis tracks the right-and-left axis of the operator and that the Y axis tracks the back-and-forth axis of the operator, detects vibration by the motion of the head of the operator to transform into an electric signal, and outputs the signal with a signal cable 88.

At this point, when the acceleration sensor 106 is the two-axis sensor, in the case where the sensor section stands vertically, the sensor is sometimes not able to detect a change of the motion by the operator. As the measures, in order for the acceleration sensor 106 to operate also in the case where the posture of the operator is upright, it is preferable that the acceleration sensor 106 is attached to the holder 7 at an angle in advance. By thus attaching, the two-axis sensor is adequate as the acceleration sensor 106, and to completely avoid the problem, it is further preferable to perform acceleration detection using three-axis data and a gyro sensor.

Further, use of a three-axis sensor for the acceleration sensor 106 enables the motion of the operator, particularly, an up-and-down motion to be detected in detail by the Y axis and Z axis, thereby improves accuracy of the application range to set, and is more effective.

An operation apparatus 107 is provided with an application range selection switch 107a that the operator operates in changing the application range, a center setting switch 107b that the operator operates in setting the center of the application range, and further, a reset switch 107c.

A position detecting section 108 detects up-and-down and right-and-left positions of the head 111 of the operator from values of acceleration of X and Y output from the acceleration sensor 106. Then, when the center setting switch 107b of the operation apparatus 107 is operated, the position detecting section 108 stores a position indicated by acceleration information at this point as the center position to output to an optical axis adjusting section 109.

The optical axis adjusting section 109 drives a drive apparatus $M_2$ based on the center position information to displace the deflection member 105, and deflects the optical axis of the light emitting device 101 in accordance with the center position. Thus, when the operator shifts the eye line from the target portion A to the target portion B and operates the center setting switch 107b in FIG. 13, the target portion B is the center position of the application range. Then, even when the operator returns the eye line from the target portion B to the target portion A, the application range is held at Sb.

When the target portion A to actually perform the medical treatment is not included in the application range Sb by deflecting the application range, the operator operates the application range selection switch 107a of the operation apparatus 107 to enlarge the application range. In response to the operation, an application control section 110 controls a drive apparatus $M_1$, adjusts tightening of the reflector 102 by the tightening member 104 in three stages, and thereby adjusts the aperture angle α. At this point, the application control section 110 controls the drive apparatus $M_1$ corresponding to the number of times the application range selection switch 107a is operated, and changes the application range.

Further, when the reset switch 107c is operated, the operation apparatus 107 outputs a reset signal R to the position detecting section 108 and application control section 110. The position detecting section 108 clears the stored acceleration information by the reset signal R, the deflection state of the optical axis by the optical axis adjusting section 109 is thereby canceled, and the application direction of the illumination section 1 is matched with the direction in which the head of the operator feces. Further, by the reset signal R being input, the application control section 110 adjusts the tightening member 104 so as to make the application range the narrowest range set as a default.

By using the acceleration sensor 106 that detects a motion of the head, it is possible to perform ON/OFF of the illumination section 1 and light quantity control. In this case, when the application range selection switch 107a and the center setting switch 107b are pressed at the same time, the position detecting section 108 outputs the acceleration information to an illumination control section 112.

By this means, the illumination control section 112 controls the illumination section 1 to increase a quantity of light by a rightward shift of the operator, while controlling the illumination section 1 to decrease a quantity of light by a leftward shift of the operator. Further, the illumination control section 112 lights the illumination section 1 by an upward shift of the head, and extinguishes the illumination section 1 by a downward shift.

In this way, the acceleration sensor 106 detects the motion of the head, the operator performs switch operation of the operation apparatus 107 as appropriate, and it is thereby possible to set the application range of the illumination section 1 and perform ON/OFF of the section and light quantity control.

Figure 1:
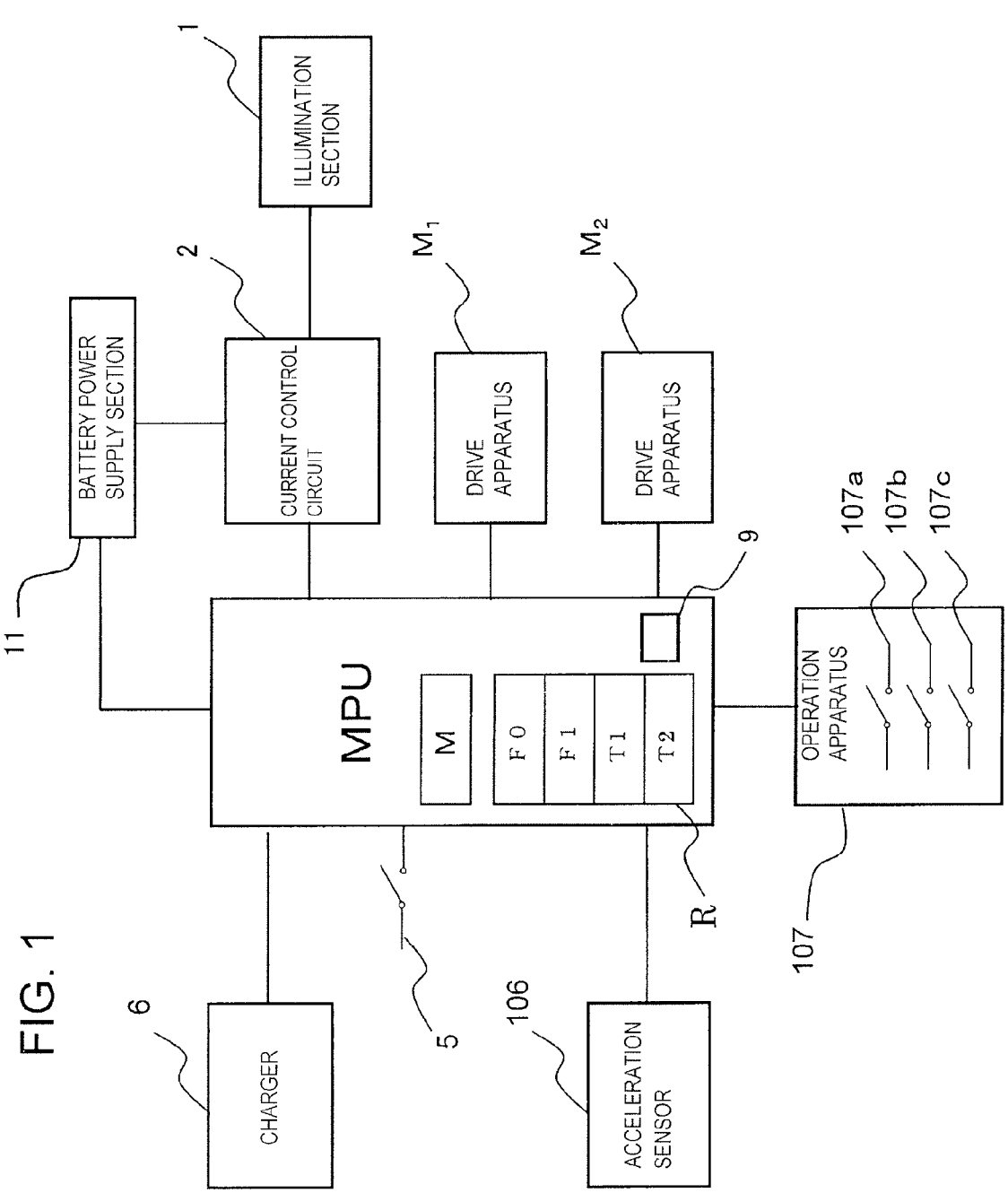
FIG. 1 is a block diagram illustrating an electric circuit of a medical light source device according to an Embodiment of the invention.

In the above-mentioned description, the control configuration of the medical light source device according to the invention is described with the functional blocks. FIG. 1 shows, in a block diagram, an electric circuit of the medical light source device according to one Embodiment of the invention, and to a microprocessor unit (hereinafter, simply referred to as an MPU) are connected a current control circuit 2, illumination switch 5 that is operated in turning ON/OFF the illumination section 1, battery power supply section 11 comprised of a plurality of connected rechargeable batteries, AC adapter as a charger 6 to charge the battery power supply section 11, acceleration sensor 106, drive apparatus $M_1$ of the tightening member 104, drive apparatus $M_2$ of the deflection member, and operation apparatus 107. As described above, the operation apparatus 107 includes the application range selection switch 107a, center setting switch 107b, and reset switch 107c. In addition, the MPU, current control circuit 2, illumination switch 5 and operation apparatus 107 are stored in the control unit 10 as described previously, and held on the body of the operator with the battery holding belt 8.

The illumination section 1 is connected to the current control circuit 2, and corresponding to a control signal from the MPU, the current control circuit 2 adjusts a passing current from the battery power supply section 11 to the illumination section 1, and thereby controls lighting and increase/decrease of the quantity of light. At this point, with the application range selection switch 107a and center setting switch 107b pressed at the same time, based on the acceleration information output by the acceleration sensor 106 after detecting the motion of the head of the operator, the MPU outputs the control signal to the current control circuit 2.

In this Embodiment, when a control signal indicative of increasing the light quantity is supplied from the MPU, the current control circuit 2 changes the average current value fed to the illumination section 1 from a rated value so as to supply a current of an increase value higher than the rated value, and causes the section 1 to emit lighter. Accordingly, in order to protect the illumination section 1 from heat, it is necessary to limit a period during which the section 1 emits with high output.

However, in the case of the light source device that the operator wears on the body, since the operator applies light by oneself, illuminance required for the operator is reserved. Further, in the case of medical use, a work time is limited which requires high precision needing to particularly increase illuminance even in an operation continuing for a long time, and therefore, even when limitations are imposed on the period to emit with high output, any practical problem does not occur. Conversely, such an device needs neither heat dissipation measures against emission with high output for a long period nor a large-capacity battery, is made compact, and is preferable as a light source device worn on the body.

The light source of the illumination section 1 is not limited to an LED element, and is only required to be a light source which does not become damaged immediately when the passing current exceeds a rated value and has durability to some extent, and, for example, there are a halogen lamp and xenon lamp. However, a normal gas-filled incandescent lamp causes damage in the filament when the passing current exceeds a rated value, and is not preferable. The halogen lamp has the tungsten filament as the incandescent lamp, but tungsten recovers to the filament, even when the lamp becomes a high temperature and tungsten sublimes, by the chemical reaction called the halogen cycle, and therefore, the halogen lamp has durability against heat. Further, the xenon lamp that does not have the filament has higher durability.

Further, the MPU checks the power supply capacity of the battery power supply section 11, and when the MPU detects a reduction in the voltage, lights an indicator 9 to warn. Then, when the charger 6 is connected to the control section 4, the control section 4 controls the current supply to charge the batteries in the battery power supply section 11 from the charger 6 and charges.

Figure 16A:
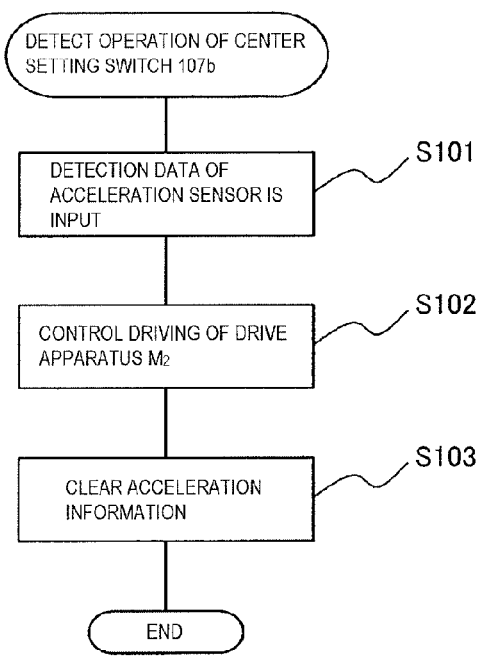
FIG. 16A is a flowchart illustrating a processing procedure for setting the application direction.

Each functional block of the position detecting section 108, optical axis adjusting section 109 and application control section 110 described in setting of the application range in FIG. 15 is programmed in a processing procedure for the MPU to set the application range. FIG. 16A shows a flowchart of a processing procedure for setting the application direction, and FIG. 16B shows a flowchart of a processing procedure for adjusting the application range.

In FIG. 16A, when the MPU detects that the center setting switch 107b is operated, the MPU performs processing of step S101, and receives acceleration data detected by the acceleration sensor 106. Then, in processing of step S102, the MPU drives the drive apparatus $M_2$ so that X and Y positions of captured acceleration data become the center position of the application range, adjusts the deflection member 105 to align the optical axis of the illumination section 1, and deflects the application direction to be a state displaced from the position of the head.

Next, in step S103, the MPU stores the acceleration information in memory M, and holds the application direction of the illumination section 1 and the direction in which the body faces always in a deflection state with a certain relationship. When the reset switch 107c is operated, the MPU clears the memory M, drives the drive apparatus $M_2$ so that X and Y positions of the optical axis are respectively "0", and cancels the deflection state.

Figure 16B:
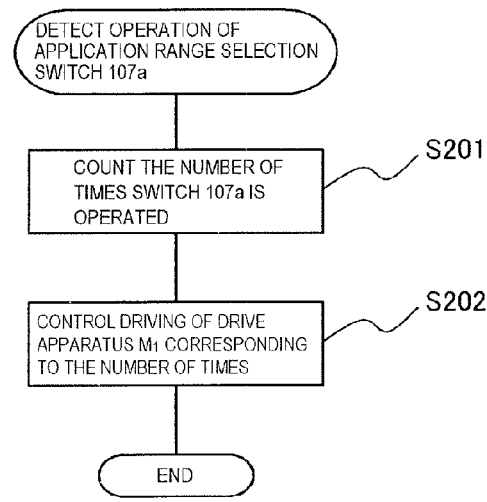
FIG. 16B is a flowchart illustrating a processing procedure for adjusting the application range.

In FIG. 16B, when the MPU detects that the application range selection switch 107a is operated, the MPU counts the number of times the switch 107a is operated in step S201, drives the drive apparatus $M_1$ corresponding to the number of times in step S202, and adjusts the tightening member 104 to enlarge the application range. When the reset switch 107c is operated, the MPU drives the drive apparatus $M_1$ so that the application range is the smallest application range.

Figure 2:
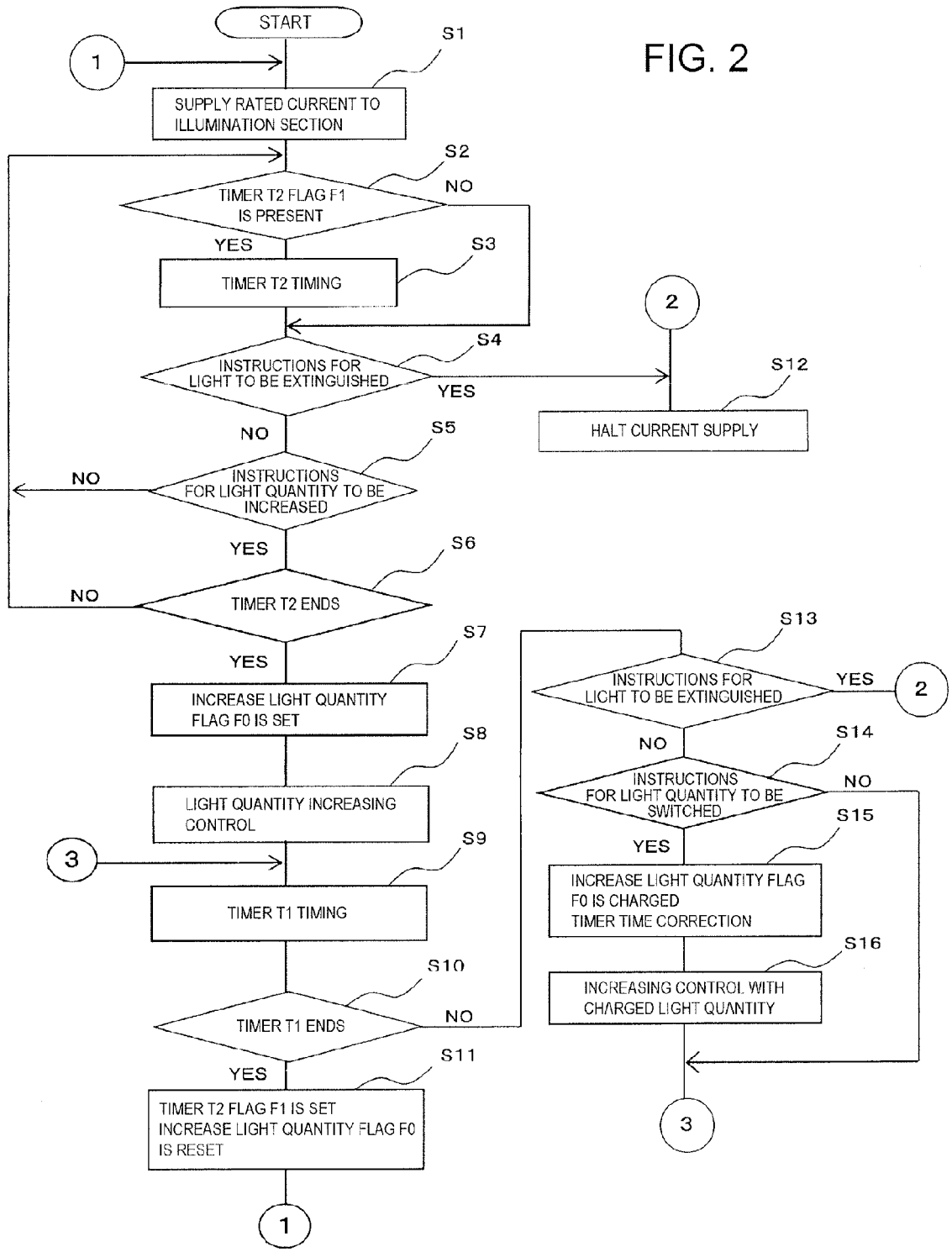
FIG. 2 is a flowchart illustrating one example of a processing procedure for a control section to control lighting of an illumination section according to the Embodiment of the invention.

Referring to a flowchart in FIG. 2, described is control for the MPU to adjust ON/OFF of the illumination section 1 and the light quantity by a motion of the head of the operator using the acceleration sensor 106. In this case, processing of a program by the MPU attains functions of a motion detecting section that detects a predetermined motion of the head by the operator based on the acceleration information from the acceleration sensor 106, and a light quantity control section that controls the current control circuit 2 to adjust an amount of current fed from the battery power supply section 11 to the illumination section 1 when the predetermined motion is detected.

First, the MPU starts the processing procedure when the MPU detects an upward motion of the head of the operator using the acceleration sensor 106 with the switches 107a and 107b of the operation apparatus 107 pressed at the same time, and controls the current control circuit 2 so as to supply a rated value of current to the illumination section 1 (step S1). The current control circuit 2 at this point is controlled by the MPU so that an average current value fed from the battery power supply section 11 to the illumination section 1 is the rated value. In addition, in this example, ON/OFF of the illumination section 1 is also performed by operation of the illumination switch 5.

Then, the MPU checks whether the register R is set for a timer T2 flag F1 (step S2), and when the flag is not set, proceeds to step S4. Meanwhile, when the flag is set, the MPU adds a timer value to the timer T2 of the register R to perform timer timing (step S3). The processing of step S2 and step S3 will be clarified later. Herein, the timer flag T2 is not set, and the MPU performs processing of step S4.

In step S4, the MPU checks whether the operator moves the head downward to give "instructions for the light to be extinguished" using the acceleration sensor 106 with the switches 107a and 107b pressed at the same time. When the head does not move downward, in next step S5, the MPU checks whether the operator moves the head rightward to give "instructions for the light quantity to be increased" with the acceleration sensor 106. When the "instructions for the light quantity to be increased" are given, the MPU checks whether the timer T2 clocking in the register R finishes (step S6). In this case, since clocking operation by the timer T2 is not performed, the MPU proceeds to next step S7, and sets the register R for an increase light quantity flag F0.

In this example, it is possible to adjust increases in the light quantity in two stages. When the operator once shifts the head to the right and further shifts the head to the right with the switches 107a and 107b pressed at the same time, a higher increased current is fed to the LED element of the illumination section 1 to cause the element to emit with the maximum light quantity. Accordingly, the MPU writes data for distinguishing whether the light quantity increase is of the first stage or the second stage in the increase light quantity flag F0.

Then, the MPU outputs a control signal to the current control circuit 2 so as to increase the light quantity from the illumination section 1 in response to the "instructions for the light quantity to be increased" (step S8). By this light quantity increasing control, the average current value fed to the illumination section 1 changes from the rated value to an increase value higher than the rated value.

When a current of the increase value higher than the rated value is fed to the illumination section 1, the LED element generates heat corresponding to a temperature increase characteristic thereof and develops a malfunction, and therefore, the time, during which the MPU feeds the current of the increase value higher than the rated value to the illumination section 1, is determined to be a predetermined period based on the temperature increase characteristic of the LED element. More specifically, the predetermined period is set so that the temperature of the LED element within the predetermined period does not exceed a maximum allowable value based on the temperature increase time characteristic of the LED element.

Accordingly, after performing the light quantity increasing control, the MPU adds a timer value to the timer T1 of the register R to perform timer T1 timing (step S9). Then, as a result of addition, the MPU determines whether the value of the timer T1 reaches a predetermined criterion value, and thereby determines whether the timer time exceeds the predetermined period (step S10). At this point, since increases of the light quantity are controlled in two stages, the predetermined period is set to be shorter in the maximum light quantity, and the MPU is programmed to vary the criterion value of the value of the timer T1 corresponding to the increase light quantity set on the increase light quantity flag F0 in step S7.

For example, in the maximum light quantity, the light quantity is increased by 40% as compared with the time of normal rated current supply, and the timer time of 20 minutes is set as the predetermined period. In increasing the light quantity in the first stage, the timer time of 30 minutes is set as the predetermined period so as to increase the light quantity by 30% as compared with the time of normal rated current supply.

In step S10, when the MPU determines that the value is within the timer time, the MPU checks whether the "instructions for the light to be extinguished" are given by a downward motion of the head (step S13), and when the "instructions for the light to be extinguished" are not given, performs the processing of from step S14. In this case, when the operator shifts the head to the right to give "instructions for the light quantity to be switched" from the light quantity increase of the first stage to the maximum light quantity or when the operator shifts the head to the left to give "instructions for the light quantity to be switched" from the maximum light quantity to the light quantity increase of the first stage, the MPU performs processing of step S15. Accordingly, the MPU rewrites the content of the increase light quantity flag F0 corresponding to the "instructions for the light quantity to be switched", while correcting a timer value of the timer T1 of the register R, subsequently in step 16 switches to emission with the light quantity indicated by the "instructions for the light quantity to be switched", and repeats the operation of from step S9. Accordingly, the increase value of current is continuously fed to the illumination section 1, and the LED element emits lighter than usual.

In thus increasing the light quantity, when the "instructions for the light to be extinguished" are given by a downward motion of the head (step S13), the MPU controls the current control circuit 2 to halt the supply of current to the illumination section 1, and finishes lighting of the illumination section 1 (step S12). Concurrently, the control section 4 all clears the content of the register R to be the initial state.

Meanwhile, when the MPU identifies an end of the timer time T1 in step S10, the MPU sets the register R for a timer T2 flag E1, while clearing the increase light quantity flag F0 (step S11), then shifts to the processing of step S1, switches the current supplied to the illumination section 1 to the rated value to switch emission of the LED element to the normal state, and performs the operation of from step S2.

Thus, when the MPU performs the processing of step S2 after once increasing the light quantity of the illumination section 1, and feeding the rated value of current again to return to the normal light quantity, since the MPU sets the register R for the timer 12 flag F1 in the processing of prior step S11, the MPU performs the processing of step S3 subsequently, and adds a timer value to the timer T2 of the register R to perform timer T2 timing. Then, the MPU checks the presence or absence of the "instructions for the light to be extinguished" from the motion of the head (step S4). When the "instructions for the light to be extinguished" are not given, the MPU next checks the presence or absence of the "light quantity increase" from the operator (step S5), and in the absence, returns to step S2.

When the MPU is given the "instructions for the light quantity to be increased" by the motion of the head of the operator in step S5, the MPU determines whether the value of the timer T2 reaches the predetermined criterion value in next step S6, and thereby determines whether the timer T2 time exceeds the predetermined period. The predetermined period at this point is the above-mentioned time required for the temperature of the LED element to fall below the rated allowable value after the increase value of current is fed to the illumination section 1.

When the timer T2 does not reach the predetermined period, the MPU performs the processing of from step S2 from this state, keeps emission of the LED element in the normal state, and performs timer T2 timing. Accordingly, within the period of the timer T2 after increasing the light quantity of the illumination section 1, and feeding the rated value of current again to return to the normal light quantity, the MPU does not feed an increase value of current even when the operator gives the "instructions for the light quantity to be increased" by a rightward shift of the head.

Then, when the timer T2 exceeds the predetermined period, the MPU clears the timer T2 flag F1 to proceed to step S7, sets the register R for the increase light quantity flag F0, and controls the current control circuit 2 so as to feed the increase value of current to the illumination section 1.

The light quantity increasing control by the above-mentioned series of control is to feed the increase value of current exceeding the rated current within a range of the timer time that guarantees prevention of deterioration of the LED element due to heat in the illumination section 1. In contrast thereto, it is also possible to prevent the LED element from deteriorating, by detecting the increased temperature of the illumination section 1 with a temperature sensor in feeding the increase value of current exceeding the rated current.

Figure 3:
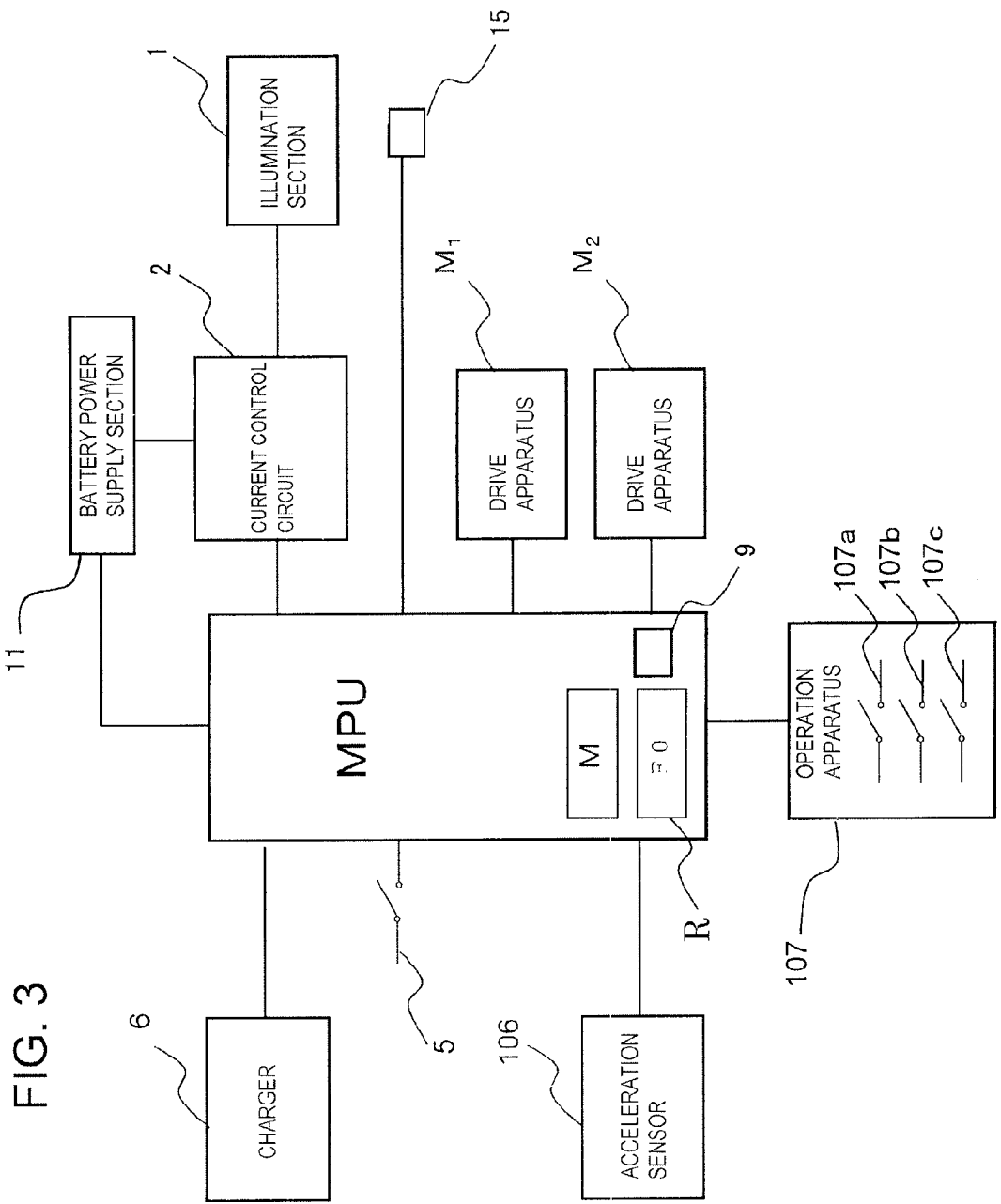
FIG. 3 is a block diagram illustrating an electric circuit of a medical light source device according to another Embodiment of the invention.
Figure 4:
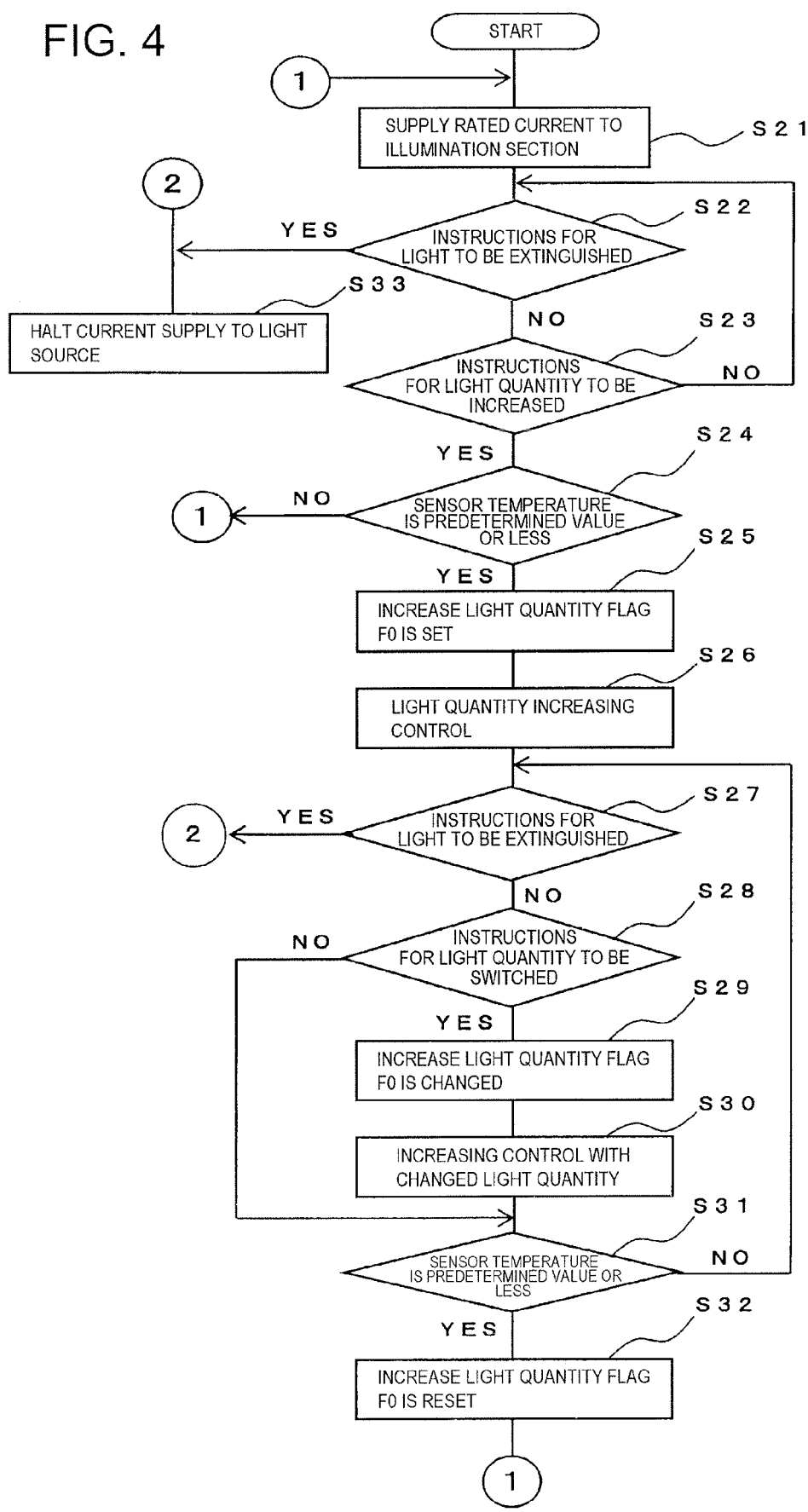
FIG. 4 is a flowchart illustrating another example of a processing procedure for a control section to control lighting of an illumination section according to another Embodiment of the invention.

FIG. 3 shows, in a block diagram, an electric circuit of a medical light source device provided with a temperature sensor, and components in the circuit having the same functions as in FIG. 1 are assigned the same reference numerals to omit descriptions thereof. In this Embodiment, a temperature sensor 15 by a thermistor or the like is provided to measure the temperature of the LED element of the illumination section 1. Referring to a flowchart in FIG. 4, described below is a processing procedure for the MPU to control lighting of the illumination section 1 in the electric circuit in FIG. 3.

The MPU starts the processing procedure when the MPU detects an upward motion of the head of the operator using the acceleration sensor 106 with the switches 107a and 107b of the operation apparatus 107 pressed at the same time, or by operation of the switch 5, and controls the current control circuit 2 so as to supply a rated value of current to the illumination section 1 (step S21). The current control circuit 2 is controlled by the MPU so that an average current value fed from the battery power supply section 11 to the illumination section 1 is the rated value.

Then, the MPU checks whether the operator gives "instructions for the light to be extinguished" by an upward shift of the head (step S22). When the "instructions for the light to be extinguished" are not given, the MPU next checks a rightward shift of the head by the operator, and thereby checks whether the operator gives "instructions for the light quantity to be increased" (step S23). In the case where the "instructions for the light to be increased" are not given, the MPU repeats the processing of from step S22. When the "instructions for the light to be extinguished" are given in step S22, the MPU performs processing of step S33, controls the current control circuit 2 so as to halt the supply of current to the illumination section 1 from the battery power supply section 11, and halts emission operation.

Meanwhile, when the MPU detects that "instructions for the light quantity to be increased" are given in step S23, the MPU captures an output from the temperature sensor 15 to detect the temperature, and determines whether the detected temperature is a predetermined temperature, for example, 80° C. in the case where the light source is an LSD element, or a lower temperature with a margin included (step S24). When the detected temperature is less than the predetermined temperature, the MPU sets the register R for an increase light quantity flag F0 (step S25). The increase light quantity flag F0 is data to identify a light quantity increase of the first stage or maximum light quantity, by whether the operator moves the head rightward once or twice.

Next, from the content of the increase light quantity flag F0, the MPU controls the current control circuit 2 so as to set the increased light quantity of the first stage or the maximum light quantity indicated by the motion of the head of the operator (step S26). By this light quantity increasing control, the average current value fed to the illumination section 1 is changed from the rated value, and the current of an increase value higher than the rated value is fed.

Then, in next step S27, the MPU checks whether the operator gives the "instructions for the light to be extinguished" by the motion of the head, and when the instructions are not given, proceeds to processing of step S28 to check whether there are instructions for an increase light quantity to be switched. In the state of performing light quantity increasing control corresponding to alight quantity increase of the first stage, when the operator shifts the head rightward, the MPU rewrites the content of the increase light quantity flag F0 to data to identify the maximum light quantity in step S29. Then, in next step S30, the MPU controls the current control circuit 2 so as to further increase the light quantity from the illumination section 1, and performs processing of step S31. Meanwhile, in the state in which the operator performs control for the maximum light quantity, when the operator shifts the head leftward, the MPU decreases the maximum light quantity to change to a light quantity increase state of the first stage.

Meanwhile, when the MPU identifies the absence of "instructions for the light quantity to be switched" in step S28, since the MPU proceeds to processing of step S31, the increase light quantity is not changed, and the emission state up to this point is maintained.

In step S31, the MPU captures an output from the temperature sensor 15 to detect the temperature, and determines whether the detected temperature is a temperature less than the predetermined temperature. When the detected temperature is the predetermined temperature or more, the MPU repeats the operator of from step S27. Accordingly, the current of the increase value of the operator flows into the illumination section 1 continuously, and the LED element emits lighter than usual in either case.

Then, when the MPU identifies that the operator gives "instructions for the light to be extinguished" by the motion of the head in step S27, the MPU performs the processing of step S33, controls the current control circuit 2 to halt the supply of the current to the illumination section 1, and finishes lighting of the illumination section 1.

In the state in which the light quantity from the LED element of the illumination section 1 is increased, when the MPU detects that the detected temperature by the temperature sensor 15 reaches the predetermined temperature in step S31, the MPU resets the increase light quantity flag F0 of the register R to perform the processing of S21, switches the supply current to the illumination section 1 to the rated value to finish the light quantity increasing control, and performs the processing of from step S22.

Then, when the MPU identifies that the operator gives "instructions for the light to be extinguished" by the motion of the head, the MPU controls the current control circuit 2 to halt the supply of the current to the illumination section 1 (step S33). At the same time, the control section 4 resets the content of the register R to be the initial state.

When the operator does not give the "instructions for the light to be extinguished", the MPU controls the current control circuit 2 to supply the rated current to the illumination section 1, and the illumination section 1 emits with the normal light quantity. Then, the MPU identifies the absence of "instructions for the light to be extinguished" in step S22, and when the MPU identifies instructions "for the light quantity to be increased" in next step S23, performs the processing of step S24. Then, the MPU captures an output from the temperature sensor 15 to detect the temperature, determines whether the detected temperature exceeds the predetermined temperature (step S24), and when the temperature is less than the predetermined temperature, sets the register R for the increase light quantity flag F0 corresponding to instructions of the light quantity increase of the first stage or the maximum light quantity by the motion of the head of the operator (step S25) to repeat the light quantity increasing control again. Accordingly, for a period during which the MPU confirms that the temperature of the LED element is less than the predetermined temperature in step S24, the MPU is capable of resuming the light quantity increase even after finishing the light quantity increase.

Control of the current supply to the illumination section 1 by the MPU in the control section 4 will be described, with specific circuit configurations of the current control circuit 2 shown. In addition, two configurations of the current control circuit 2 are exemplified in FIGS. 5 and 6, and the current control circuit 2 in either Embodiment of FIG. 1 or FIG. 2 may also be used.

Figure 5:
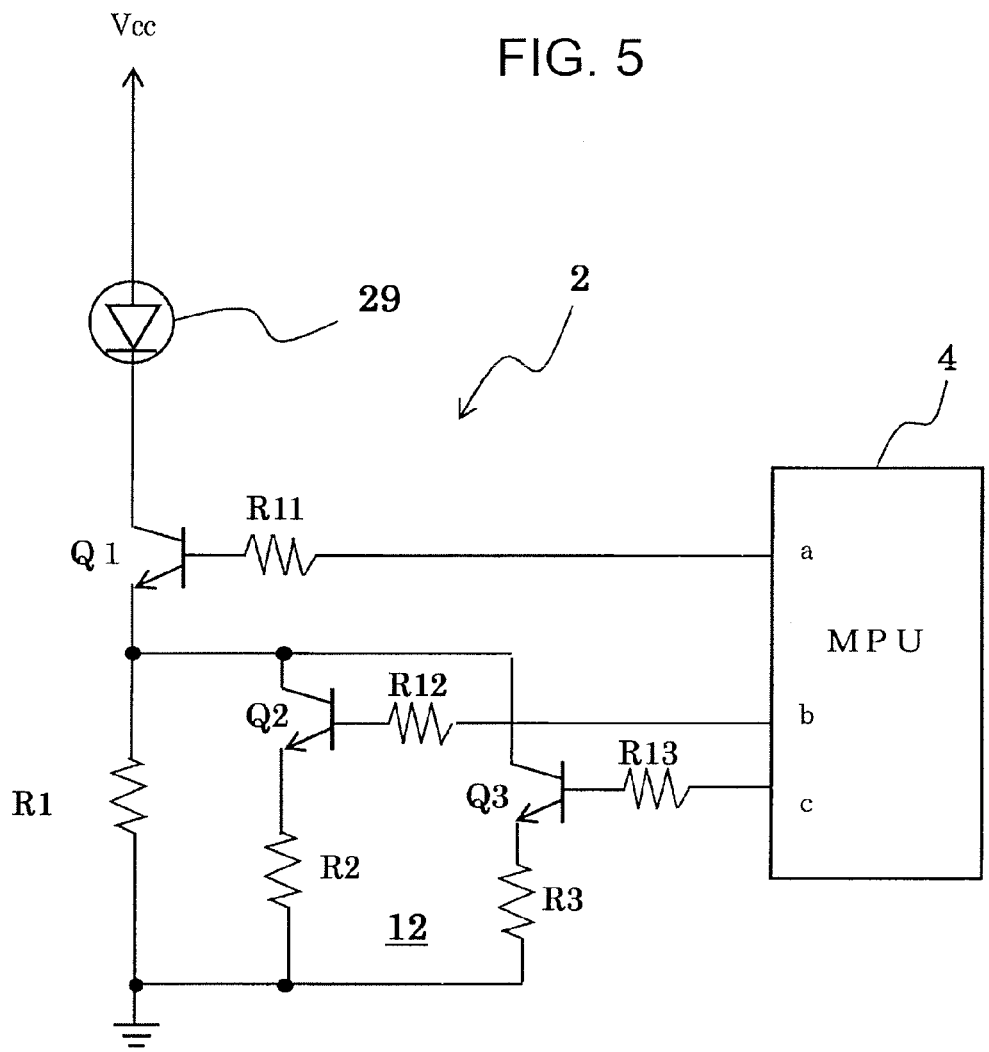
FIG. 5 is a diagram illustrating a specific circuit configuration showing an example of a current control circuit according to the Embodiment of the invention.

The current control circuit 2 as shown in FIG. 5 is constructed by connecting a driving transistor Q1 connected on its collector side to the LED element 29 that is a light source of the illumination section 1, and a resistance circuit 12 connected to the emitter side of the transistor Q1 to power supply Vcc. Then, the MPU is connected at a port a to the base of the transistor Q1 through a resistance R11, and controls ON/OFF of the transistor.

The resistance circuit 12 is comprised of a resistance R1 connected at its one end to the emitter of the transistor Q1 with the other end grounded, a series circuit of a transistor Q2 and resistance R2 parallel connected to the resistance R1, and a series circuit of a transistor Q3 and resistance R3 also parallel connected to the resistance R1. Then, the base of the transistor Q2 is connected to a port b of the control section 4 through a resistance R12, the base of the transistor Q3 is connected to a port c of the control section 4 through a resistance R13, and the control section 4 controls ON/OFF of each transistor. Herein, the resistance R11, resistance R12 and resistance R13 are provided to limit the base current to respective connected transistors.

A resistance value of the resistance circuit 12 is determined by a combined resistance value of the resistances R1, R2 and R3, and the current limitation resistance value is R1 in the normal state in which the transistor Q2 and the transistor Q3 are off, is $R1 \cdot R2/(R1+R2)$ when the transistor Q2 is on and the transistor Q3 is off, and is $R1 \cdot R2 \cdot R3/(R1+R2+R3)$ when the transistor Q2 and the transistor Q3 are both on.

At this point, the resistance values of the resistances R1, R2 and R3 are set such that $R1 > R1 \cdot R2/(R1+R2) > R1 \cdot R2 \cdot R3/(R1+R2+R3)$, the supply current to the LED element 29 is the rated value when the resistance value is R1, the supply current when the current limitation resistance value is $R1 \cdot R2/(R1+R2)$ is an increase value, and the supply current when the current limitation resistance value is $R1 \cdot R2 \cdot R3/(R1+R2+R3)$ is further increased. By this means, when the control section 4 switches off both the transistor Q2 and the transistor Q3, the rated value of current is supplied to the LED element 29 and the emission amount is normal. When the transistor Q2 is switched on, an increase value of current is supplied and the emission amount is increased. When both the transistor Q2 and the transistor Q3 are switched on, the supply current is higher, and the emission amount increases.

Accordingly, when the MPU detects that the head of the operator shifts upward by the acceleration sensor 106 with the switches 107a, 107b pressed at the same time, the MPU switches off the transistor Q2 and the transistor Q3. Then, when the MPU detects that the head of the operator shifts rightward once, the MPU switches on the transistor Q2, and when the MPU detects that the head of the operator shifts rightward twice, the MPU switches on both the transistor Q2 and the transistor Q3.

In the current control circuit 2 of such a configuration, when the MPU switches on the transistor Q1 to supply power supply Vcc to the current control circuit 2, the current is fed to the LED element 29. At this point, since the control section 4 keeps the transistor Q2 and the transistor Q3 off, the rated current is fed to the LED element 29, and normal emission is performed. In addition, the MPU controls on/off of the transistor Q1 with a predetermined duty ratio to feed a predetermined current. Accordingly, the voltage applied to the LED element 29 is of a rectangular wave form, but is not limited to the rectangular wave, and may be substantially a half wave form by making the rising edge and the falling edge the shape of steps. By this means, it is possible to resolve abrupt illuminance changes.

Then, when the MPU detects the motion of the head of the operator and switches on the transistor Q2 or switches on both the transistor Q2 and the transistor Q3, the current corresponding to the current limitation resistance value of the resistance circuit 12 is fed to the LED element 29, and the LED element emits. Accordingly, when the MPU detects that the head of the operator shifts rightward once or twice during the illumination operation of the illumination section 1 with the rated current, the MPU controls the illumination section 1 so that an amount of current exceeding the rated current is fed to the LED element. Thus, the control section 4 controls the transistors Q1, Q2 and Q3 from the ports a, b and c, and switches the emission amount of the LED element 29.

Controlling the emission operation of the illumination section 1 is not limited to the above-mentioned circuit configuration, and may be a pulse driving scheme for controlling a duty ratio corresponding to designation of the illumination intensity with a switch device such as, for example, a transistor and MOSFET, on the circuit and thereby controlling a current fed to the illumination section 1.

Figure 6:
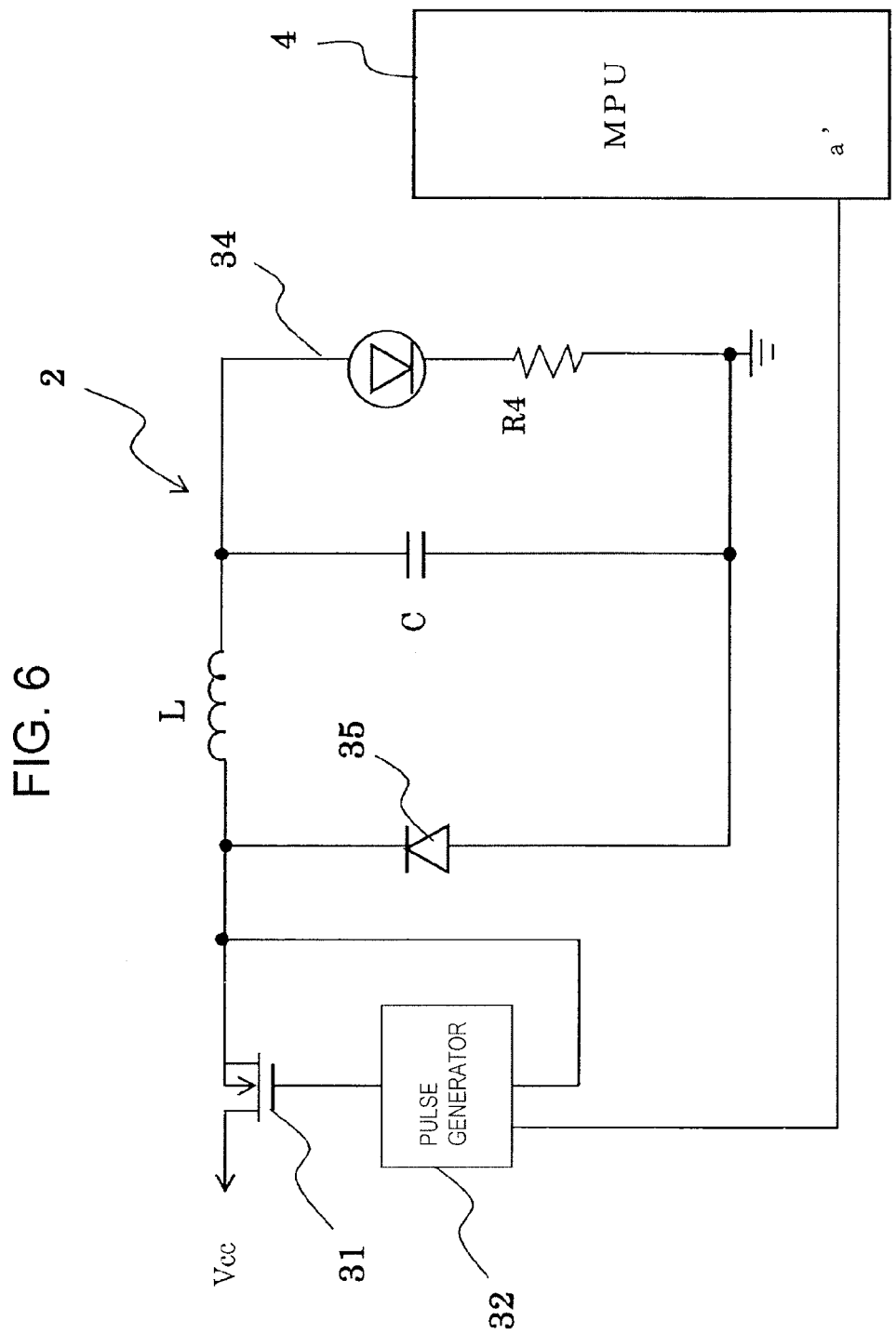
FIG. 6 is a diagram illustrating a circuit configuration with a pulse driving scheme adopted in the current control circuit according to the Embodiment of the invention.

FIG. 6 shows a configuration of the current control circuit 2 by the pulse driving scheme. In FIG. 6, for example, MOSFET is used as a switch device 31, and is connected so that a PWM (Pulse Width Modulation) signal from a pulse generator 32 is input to the gate side thereof. When the PWM signal becomes a high level by a control signal from a port a' of the control section 4, the switch device 31 is turned on, the voltage of the battery power supply section 11 is applied, and the current flows from the input side to the load side.

To the load side of the switch device 31 are connected an LED 34 of the illumination section 1 and a protective resistance R4 which is grounded. In the prior stage, a smoothing circuit comprised of a coil L and a capacitor C is provided, and it is configured that a pulse output by switching operation is averaged and output. In the stage before the coil L, a diode 35 is provided to continue to supply a current to the coil L when the switch device 31 is switched off. By this means, by controlling the on time (off time) of the switch device 31, it is possible to adjust the current fed to the illumination section 1. Accordingly, in this case, the control section 4 is capable of increasing the light quantity of the illumination section 1 by performing control for changing the duty ratio of the pulse generator 32. In addition, the voltage applied to the LED element 29 is of a rectangular wave form, but is not limited to the rectangular wave, and may be substantially a half wave form by making the rising edge and the falling edge the shape of steps.

When the MPU detects that the head of the operator shifts rightward once or twice by the acceleration sensor 106 with the switches 107a, 107b pressed at the same time, the MPU performs the control for changing the duty ratio so that the average current value fed to the illumination section 1 is changed from the rated value and that an increase value of current higher than the rated value is fed. Then, when the operator shifts the head rightward twice, the MPU makes the fed current higher than in shifting once.

In the medical light source device according to the above-mentioned Embodiment, by using the acceleration sensor 106 that detects a motion of the head, it is made possible to set the application range of the illumination section 1 and perform ON/OFF and light quantity control, and ON/OFF and light quantity control may be performed using a voice recognition technique. In this case, by providing a switching switch for switching between a voice mode and an acceleration mode, it is possible to use both the acceleration sensor 106 and the voice recognition technique.

Figure 11:
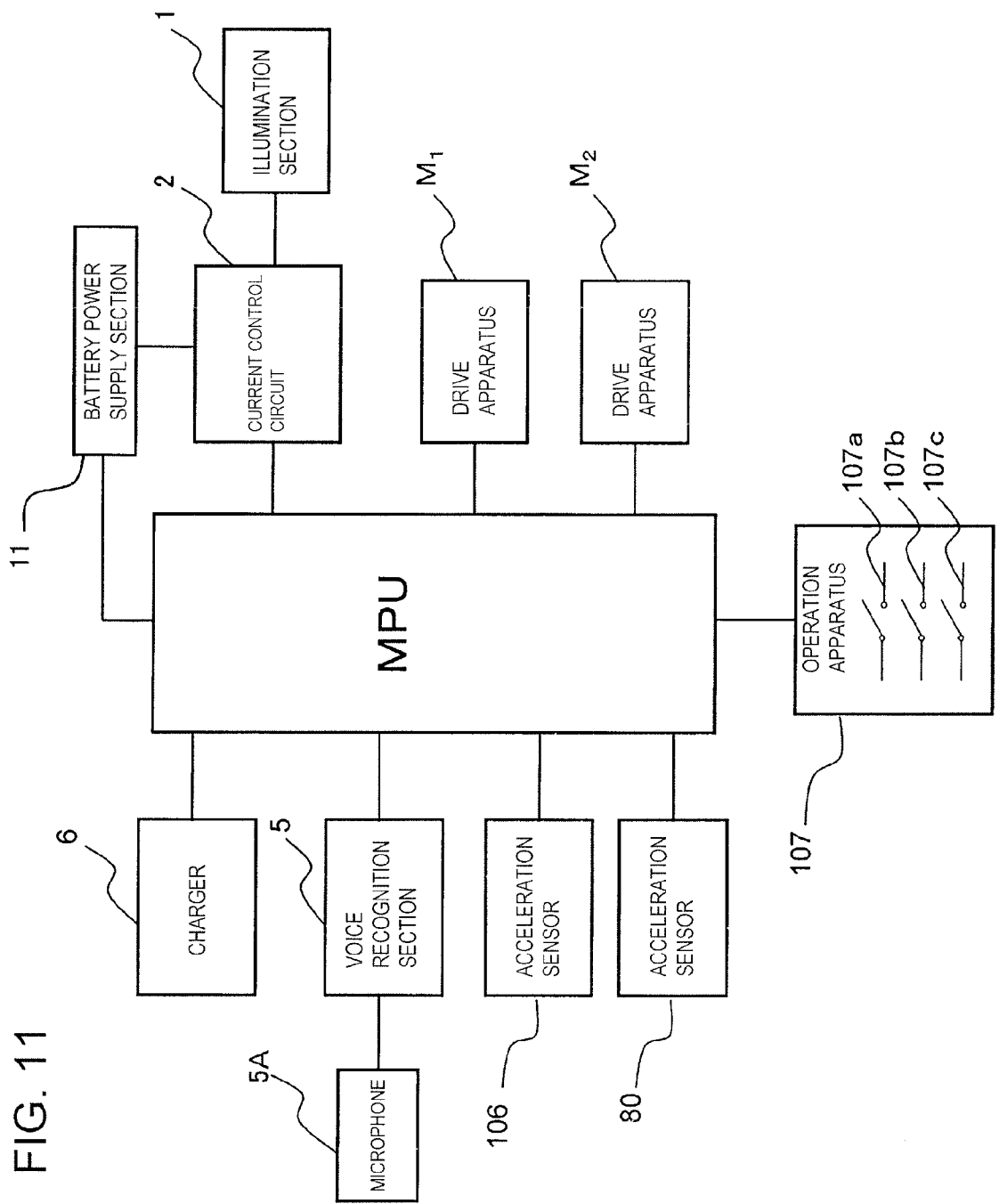
FIG. 11 is a block diagram illustrating an electric circuit of a medical light source device in the case of performing ON/OFF of an illumination section 1 and light quantity control using a voice recognition technique.

FIG. 11 shows a configuration of a medical light source device in the case of performing ON/OFF of the illumination section 1 and light quantity control using the voice recognition technique, and components of the circuit having the same functions as in FIG. 1 are assigned the same reference numerals to omit descriptions thereof.

In FIG. 11, a voice recognition section 5 is capable of recognizing about several kinds of voices using the conventional publicly-known general voice recognition technique. For example, with the voice recognition section 5 are registered voice patterns of several kinds of words required to indicate "light", "extinguish", "lighter", "lightest" and the like, and the section 5 is configured to compare a signal of voice uttered by the operator collected in a microphone 5A to recognize the content. When a command signal indicated by the voice is input from the voice recognition section 5, the MPU outputs a control signal to the current control circuit 2 according to the command content.

In other words, when the voice recognition section 5 recognizes a voice of "light", the MPU outputs a control signal to supply a normal rated current from the battery power supply section 11 to the illumination section 1, and light the illumination section 1. Then, when the voice recognition section 5 recognizes a voice of "lighter", the MPU outputs a control signal to the current control circuit 2 so as to change the average current value fed to the illumination section 1 from the rated value and supply the increase value higher than the rated value. When the section 5 recognizes a voice of "lightest", the MPU outputs a control signal to the current control circuit 2 so as to change the average current value fed to the illumination section 1 to a higher increase value to supply.

The voice recognition section 5 and microphone 5A are integrated into a single unit, and are stored in the control unit 10 together with the MPU and current control circuit 2, and it may also be configured that the microphone 5A is separated from the voice recognition section 5, is placed near the mouth or the chest of the operator, and is connected to the voice recognition section 5 by wireless or cable. For example, in the head band that is the holder 7 of the illumination section 1 as shown in FIG. 9, the microphone 5A is attached together with the illumination section so as to position near the mouth of the operator.

Further, the medical light source device as shown in FIG. 11 controls an emission amount of the illumination section 1 from a motion of the operator using the acceleration sensor. In this case, it is preferable to provide a second acceleration sensor to control an emission amount independently of the acceleration sensor 106. A second acceleration sensor 80 is attached to the holder worn on the body of the operator as in the acceleration sensor 106, but may be a uniaxial sensor only to detect a motion of the operator.

In medical operations, it is assumed that the time with the need for applying a higher quantity of light to a part in the medical treatment such as, for example, cutting and suture of a blood vessel or minute portion and the like is almost 20% of the whole, and by controlling to dim the illumination section 1 during a period except the time of almost 20%, it is possible to suppress consumption of the power supply. Accordingly, when the time is judged as being not during the medical operation from the motion of the operator detected by the acceleration sensor, the supply current to the illumination section 1 is switched to the rated value. By this means, in a state in which the average current value fed to the illumination section 1 is set to be changed from the rated value so as to feed the current of the increase value higher than the rated value, the current value is switched to the rated value, and it is thereby possible to suppress consumption of the power supply.

In the medical treatment such as cutting and suture of a blood vessel or minute portion in an operation, the operator fixes the illumination section 1 to concentrate light on the treatment target portion, and therefore, does not make a large motion. Accordingly, the acceleration, which is detected by the acceleration sensor 80 held by the holder together with the illumination section 1, is small, and the MPU causes the section 1 to emit with the intensity required by the operator.

Meanwhile, even in the operation, during the time the operator does not perform the medical treatment directly, since the operator makes a large motion such that the operator shifts the entire body by preparation working and the like, the acceleration detected by the acceleration sensor 80 is large. Then, when the acceleration is a predetermined value or more, the MPU controls the current control circuit 2 to reduce illuminance of the illumination section 1, and effective use of the battery power supply section 11 is thereby made. At this point, when the acceleration detected by the acceleration sensor 80 is the predetermined value or more, illumination of the illumination section 1 may be halted.

Figure 12:
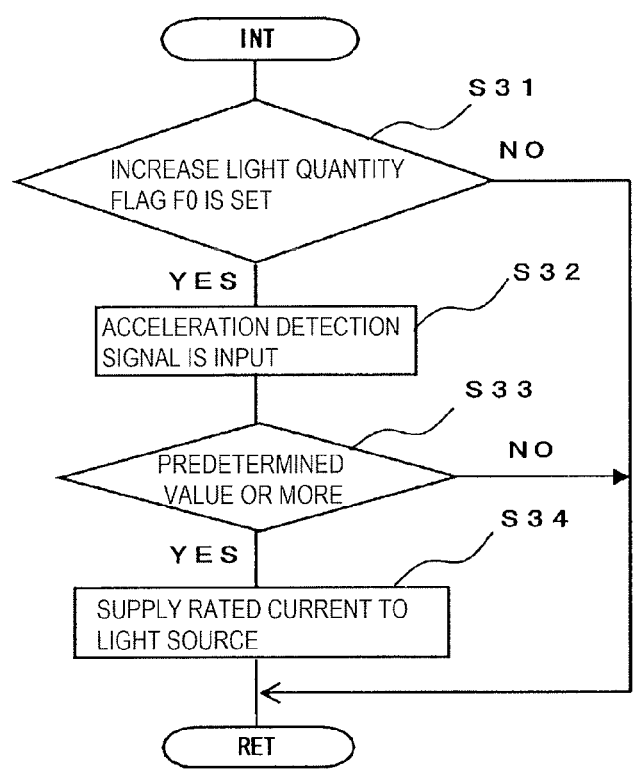
FIG. 12 is a flowchart illustrating a processing procedure of an interrupt by a timer interrupt of an MPU when an acceleration sensor is provided.

Described is operation of the MPU in the case of controlling the emission amount with the acceleration sensor 80. The MPU during the execution of the processing procedure by the flowchart in FIG. 2 or 3 periodically monitors an acceleration detection signal from the acceleration sensor 80 by timer interrupt. FIG. 12 is a flowchart illustrating the operation in interrupt processing of the MPU at the timer interrupt. The MPU checks whether the increase light quantity flag F0 (FIG. 1, FIG. 2) is set in step S31, and when the flag is not set, returns to the processing prior to the timer interrupt.

Meanwhile, when the increase light quantity flag F0 is set, in this case, the MPU is controlling the current control circuit 2 so as to feed the current of the increase value exceeding the rated current to the LED element, and performs the processing of step S32. Then, the MPU captures a detection signal from the acceleration sensor 80 to determine whether the signal value from the acceleration sensor 80 is a predetermined value or more (step S33). At this point, when the operator makes a large motion and performs work except the medical treatment, the signal value is the predetermined value or more, and the MPG controls the current control circuit 2 so as to drop the average current value fed to the illumination section 1 to the rated value to decrease illuminance of the illumination section 1 (step S34), and returns to the processing prior to the timer interrupt.

Meanwhile, when the signal value from the acceleration sensor 80 is less than the predetermined value, the MPG recognizes that the operator does not make a large motion and is during the operation, and that there is no need for decreasing illuminance of the illumination section 1, and returns to the processing prior to the timer interrupt.

By adding such interrupt processing by the timer interrupt, in feeding the current exceeding the rating of the illumination section 1 to increase the light quantity, when the operator does actually not perform the medical treatment such as concentrating light on the treatment target portion, the MPU is capable of returning to normal emission control, being effective at preventing consumption of power of the battery power supply section 11 and protecting the illumination section 1.

INDUSTRIAL APPLICABILITY

The present invention relates to the medical light source device which is attached to the body of the operator, and which enables the direction in which the body faces and the application direction of light to be set in a displaced state when necessary where the direction in which the body faces and the application direction are usually matched, and has industrial applicability.

DESCRIPTION OF SYMBOLS

1 Illumination section
2 Current control circuit
5 Voice recognition section
5A Microphone
7 Holder
11 Battery power supply section
80 Acceleration sensor
106 Acceleration sensor
107 Operation apparatus
107c Reset switch (reset means)
108 Position detecting section
109 Optical axis adjusting section
110 Application control section

The invention claimed is:

1. A medical light source device that is worn on the body of an operator to apply light to a target portion of the medical treatment, comprising:
   a holder to put an illumination section on the body of the operator;
   an acceleration sensor attached to the holder;
   a position detecting section that detects a center position to hold based on acceleration information detected by the acceleration sensor in setting the center position of an application range; and
   an optical axis adjusting section that sets an optical axis of the illumination section at the detected center position.

2. The medical light source device according to claim 1, further comprising:
   an application control section capable of adjusting an application angle of application light from the illumination section in a plurality of stages.

3. The medical light source device according to claim 1, wherein the holder is to put the illumination section and the acceleration sensor on the head of the operator.

4. The medial light source device according to claim 1, wherein the acceleration sensor has an X axis and a Y axis that are mutually orthogonal, and is attached to the holder so that the X axis tracks a right-and-left axis of the operator and that the Y axis tracks a back-and-forth axis of the operator.

5. The medical light source device according to claim 4, wherein the acceleration sensor is attached to the holder while being beforehand provided with a predetermine angle with respect to a vertical direction.

6. The medial light source device according to claim 4, wherein the acceleration sensor is a three-axis sensor further including a Z axis.

7. The medical light source device according to claim 1, further comprising:
- reset means for clearing the center position held in the position detecting sensor to cancel setting of the optical axis.

8. A medical light source device that is worn on the body of an operator to apply light to a target portion of the medical treatment, comprising:
- a holder to put an illumination section on the body of the operator;
- a battery power supply section that supplies power to the illumination section;
- an acceleration sensor attached to the holder;
- a motion detecting section that detects a predetermined motion by the operator based on acceleration information; and
- a light quantity control section that controls an amount of current fed from the battery power supply section to the illumination section when the predetermined motion is detected.

9. The medical light source device according to claim 8, wherein the illumination section is provided with a light source having durability even when a passing current exceeds a rated value, and the light quantity control section changes an average current value fed from the battery power supply section to the illumination section from a rated value to an increase value higher than the rated value only for a predetermined period in increasing the amount of current.

10. The medical light source device according to claim 9, wherein the predetermined period is set based on a temperature increase time characteristic of the light source due to passage of the increase value of current.

11. The medical light source device according to claim 9, wherein the predetermined period is set at a period during which a temperature of the light source does not exceed a maximum allowable value, based on the temperature increase time characteristic of the light source.

12. The medical light source device according to claim 9, wherein a second acceleration sensor is attached to the holder, and the light quantity control section switches a value of current fed to the illumination section to the rated value of current when the acceleration sensor detects acceleration of a predetermined value or more, in performing control for feeding the increase value of current as the average current value fed to the illumination section.

13. The medical light source device according to claim 8, further comprising:
- a voice recognition section that recognizes a voice uttered by the operator,
- wherein the light quantity control section controls the amount of current fed to the illumination section based on either the recognized voice in the voice recognition section or the acceleration information.

* * * * *